(12) United States Patent
Chemburkar et al.

(10) Patent No.: US 8,288,565 B2
(45) Date of Patent: Oct. 16, 2012

(54) PROCESS FOR THE SYNTHESIS OF (2S,3AR,7AS)-OCTAHYDRO-1H-INDOLE CARBOXYLIC ACID AS AN INTERMEDIATE FOR TRANDOLAPRIL

(75) Inventors: Sanjay R. Chemburkar, Gurnee, IL (US); Rajarathnam E. Reddy, Gurnee, IL (US); Douglas M. Reamer, Brookfield, WI (US); John T. Pavlina, Pleasant Prairie, WI (US); Stephen S. Ulrey, Lake Bluff, IL (US); Brian J. Kotecki, Oak Creek, WI (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 12/837,686

(22) Filed: Jul. 16, 2010

(65) Prior Publication Data

US 2011/0065930 A1 Mar. 17, 2011

Related U.S. Application Data

(60) Provisional application No. 61/226,030, filed on Jul. 16, 2009.

(51) Int. Cl.
*C07D 209/04* (2006.01)
(52) U.S. Cl. .................................... 548/452
(58) Field of Classification Search .................... 548/452
See application file for complete search history.

(56) References Cited

U.S. PATENT DOCUMENTS

| | | | |
|---|---|---|---|
| 4,490,386 A | 12/1984 | Seamans et al. | |
| 4,879,392 A | 11/1989 | Brion et al. | |
| 4,933,361 A | 6/1990 | Urbach et al. | |
| 6,559,318 B1 | 5/2003 | Ebel et al. | |
| 2009/0069574 A1 | 3/2009 | Kankan et al. | |

FOREIGN PATENT DOCUMENTS

| | | |
|---|---|---|
| EP | 88341 B1 | 7/1987 |
| EP | 1724260 B1 | 2/2008 |
| WO | WO8601803 A1 | 3/1986 |
| WO | WO0040555 A1 | 7/2000 |
| WO | WO2004065368 A1 | 8/2004 |
| WO | WO2004101515 A1 | 11/2004 |
| WO | WO2005051909 A1 | 6/2005 |
| WO | WO2005054194 A1 | 6/2005 |
| WO | WO2006014916 A2 | 2/2006 |
| WO | WO2006085332 A1 | 8/2006 |
| WO | WO2007003947 A2 | 1/2007 |
| WO | WO2009015166 A1 | 1/2009 |

OTHER PUBLICATIONS

Blankley C.J., et al., "Synthesis and Structure-Activity Relationships of Potent New Angiotensin Converting Enzyme Inhibitors Containing Saturated Bicyclic Amino Acids," Journal of Medicinal Chemistry, 1987, vol. 30 (6), pp. 992-998.
Brion F., et al., "Steroselective Synthesis of a trans-Octahydroindole Derivative, Precursor of Trandolapril (RU 44 570), an Inhibitor of Angiotensin Converting Enzyme," Tetrahedron Letters, 1992, vol. 33 (34), pp. 4889-4892.
Cimarelli C., et al., "Diastereo and Enantioselective Entry to Beta-Amino Esters by Hydride Reduction of Homochiral Beta-Enamino Esters," Tetrahedron Asymmetry, 1994, vol. 5 (8), pp. 1455-1458.
Hayashi Y., et al., "A Novel Chiral Super-Lewis Acidic Catalyst for Enantioselective Synthesis," Journal of the American Chemical Society, 1996, vol. 118, pp. 5502-5503.
Henning R., et al., "Coupling of Beta-Acetamido Radicals with Alpha-Chloro Acrylonitrile Anew Access to Disubstituted Proline Derivatives," Tetrahedron Letters, 1983, vol. 24 (48), pp. 5343-5346.
Henning R., et al., "Diastereoselective Synthesis of Bicyclic Amino Acids Via Ring Contraction of Alpha-Chlorolactams," Tetrahedron Letters, 1983, vol. 24 (48), pp. 5339-5342.
International Search Report and Written Opinion for Application No. PCT/US2010/042219, mailed on Nov. 22, 2010, 9 pages.
Schinnerl M., et al., "Asymmetric Synthesis of a New Helix-Forming Beta-Amino Acid; trans-4-Aminopiperidine-3-carboxylic Acid," European Journal of Organic Chemistry, 2003, vol. 2, pp. 721-726.
Xu D., et al., "A Practical Synthesis of Enantiopure Ethyl Cis-2-amino-1-Cyclohexanecarboxylate Via Asymmetric Reductive Amination Methodology," Tetrahedron Asymmetry, 1997, vol. 8 (9), pp. 1445-1451.

*Primary Examiner* — Robert Havlin
(74) *Attorney, Agent, or Firm* — Lisa V. Mueller; Michael Best & Friedrich LLP

(57) ABSTRACT

A process for the preparation of (2S,3aR,7aS)-octahydro-1H-indole-20carboxylic acid hydrochloride.

17 Claims, 6 Drawing Sheets

PROCESS FOR THE SYNTHESIS OF (2S,3AR,7AS)-OCTAHYDRO-1H-INDOLE CARBOXYLIC ACID AS AN INTERMEDIATE FOR TRANDOLAPRIL

CROSS REFERENCE TO RELATED APPLICATIONS

This application claims priority from U.S. Provisional Application Ser. No. 61/226,030 filed Jul. 16, 2009, which is incorporated herein by reference.

FIELD OF THE INVENTION

The present invention relates to an improved, stereospecific process for the manufacture of (2S,3aR,7aS)-octahydro-1H-indole-2-carboxylic acid as a hydrochloride salt, a key intermediate in the preparation of trandolapril.

BACKGROUND OF THE INVENTION

Trandolapril (1) [CAS Registry No. 87679-37-6] is the ethyl ester prodrug of trandolaprilat (2) [CAS Registry No. 87679-71-8], and it is a commonly prescribed cardiovascular drug for controlling and managing hypertension. It functions as an inhibitor of Angiotensin Converting Enzyme [ACE], which results in lowering blood pressure and is useful for treatment of heart failure. Trandolapril (1) can be used alone as oral drug. Alternatively, it can be used in combination with Verapamil, a calcium channel blocker, or with diuretics.

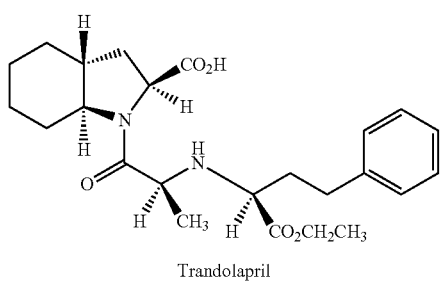

Trandolapril (1)

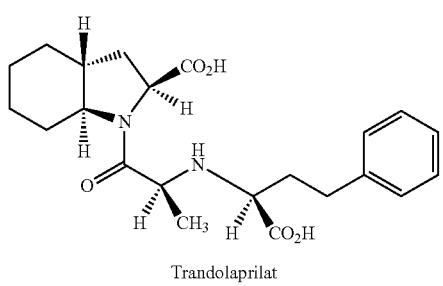

Trandolaprilat (2)

Pharmaceutical utility of trandolapril (1) for use as ACE inhibitor was first disclosed in U.S. Pat. No. 4,933,361. The general approach for preparing trandolapril (1) is based on the reaction of (2S,3aR,7aS)-benzyl octahydro-1H-indole-2-carboxylate hydrochloride (3) with (S)-2-((S)-1-ethoxy-1-oxo-4-phenylbutan-2-ylamino)propanoic acid (4) in the presence of a variety of coupling reagents to facilitate amide bond followed by hydrogenolysis of the benzyl ester. These coupling approaches to make trandolapril (1) are disclosed in U.S. Pat. No. 4,933,361 along with WO2004/101515, WO2005051909 WO2006/014916, WO2006/085332, EP 1724260, WO2007/003947 and US2009/0069574. Thus, it has been demonstrated that (2S,3aR,7aS)-benzyl octahydro-1H-indole-2-carboxylate hydrochloride salt (3) is a key component in this coupling reaction to manufacture trandolapril (1), and it is typically prepared from (2S,3aR,7aS)-octahydro-1H-indole-2-carboxylic acid (5) and benzyl alcohol.

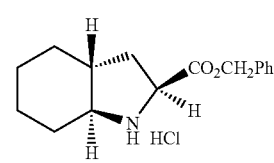

(3)

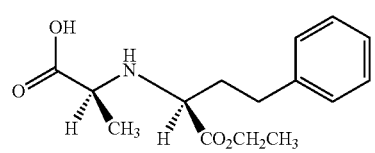

(4)

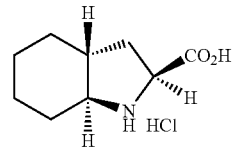

(5)

Synthesis of (2S,3aR,7aS)-octahydro-1H-indole-2-carboxylic acid (5), which contains a trans-fused octahydroindole ring system, requires correct stereochemistry at the (2S)-carboxylic acid position to afford trandolapril (1). A number of methods have been disclosed for the synthesis of (5), which involve the use of animal source materials, such as pork liver, or hazardous chemical reagents, such as bromine and sodium cyanide, or optically active reagents for resolution of racemic mixtures (which can result in low yields), and are therefore not amenable for use in large scale preparation.

For instance, the synthesis described by Henning et al., *Tetrahedron Lett.* 1983, 24, 5339 is based on Favorski type ring contraction of halogenated trans-fused system, but gives a mixture of isomers. A different method described by Henning et al., in *Tetrahedron Lett.* 1983, 24, 5343 introduces trans-fused ring system efficiently but requires the use of hazardous reagent mercuric nitrate. Further, synthesis described by Brion et al. U.S. Pat. No. 4,879,392 and *Tetrahedron Lett.*, 1992, 33, 4889 uses animal source reagent such pig liver esterase and require further chiral enrichment. WO 00/40555 and U.S. Pat. No. 6,559,318 rely on enzymatic resolution of 2-(2',2'-methoxy ethyl)cyclohexylamine and require further chromatographic separation.

Other patents and patent applications such as U.S. Pat. No. 4,490,386, EP0088341 and US2009/0069574 describe a method, which uses α-1-phenylethyl amine for resolution of N-benzoyl (2S,3aR,7aS)-octahydro-1H-indole-2-carboxylic acid.

On the other hand, WO8601803, WO2004065368 and WO2006/014916 describe the preparation of (2S,3aR,7aS)-octahydro-1H-indole-2-carboxylic acid esters via resolution using 10-D-camphor sulfonic acid. In addition, WO2005/054194 and WO2006/085332 describes the preparation of (2S,3aR,7aS)-octahydro-1H-indole-2-carboxylic acid esters via resolution using (−)-dibenzoyl-L-tartrate. Finally, EP1724260 utilizes N-acetoxy-β-acyloxy alanine ester and its addition to an enamine followed by ring closure.

As described therein, these methods can be inefficient, expensive and do not result in high yield and/or high purity production of (2S,3aR,7aS)-octahydro-1H-indole-2-carboxylic acid (5). Therefore, in accordance with the present invention, there is a need for a process that is best suited for large scale preparation of (2S,3aR,7aS)-octahydro-1H-indole-2-carboxylic acid (5) that will reduce costs, decrease the number of manufacturing steps, decrease hazardous environmental waste, and increase efficiency of the manufacturing of (2S,3aR,7aS)-octahydro-1H-indole-2-carboxylic acid (5) and ultimately trandolapril.

SUMMARY OF THE INVENTION

The present invention provides commercially scalable processes for the preparation of (2S,3aR,7aS)-octahydro-1H-indole-2-carboxylic acid hydrochloride (5). Selective N-alkylation of (1S,2S)-2-[(S)-1-phenylethyl amino]cyclohexyl)methanol (11) with ethyl bromoacetate (12) was performed with sodium bicarbonate in acetonitrile to give compound (13). The hydroxyl functionality in compound (13) is then converted to methanesulfonate ester to afford compound (14). Subsequent treatment of compound (14) with a base, such as, but not limited to, sodium tert-butoxide in tetrahydrofuran or mixtures of tetrahydrofuran produces a trans-fused octahydroindole ring system (15) with the correct stereochemistry at the (2S)-carboxylic ester position, as the major isomer. The N-α-methylbenzyl group in (2S,3aR,7aS)-Ethyl 1-((S)-1-phenylethyl)octahydro-1H-indole-2-carboxylate (15) is cleaved by hydrogenolysis using palladium on carbon or palladium hydroxide on carbon in the presence of hydrogen gas, ethanol, and hydrogen chloride, to afford the hydrochloride salt of compound (16). Thereafter, the hydrochloride salt of compound (16) is subjected to acid hydrolysis by the incorporation of hydrochloric acid to provide the (2S,3aR,7aS)-octahydro-1H-indole-2-carboxylic acid (5) as its hydrochloride salt in good overall yield (See FIG. 5). Compound (5) is isolated by crystallization from acetonitrile.

In another embodiment, (1S,2S)-2-[(S)-1-phenylethyl amino]cyclohexyl)methanol (11) is produced from a starting material comprising ethyl 2-oxocyclohexane carboxylate (6). This embodiment comprises reacting ethyl 2-oxocyclohexane carboxylate (6) with (S)-(–)-1-phenylethylamine (7) in the presence of toluene to produce (S)-Ethyl 2-(1-phenylethylamino)cyclohex-1-enecarboxylate (8). Further, reduction of the amine (8) with sodium borohydride in the presence of isobutyric acid will produce (1R,2S)-Ethyl 2-((S)-1-phenylethylamino)cyclohexanecarboxylate (9), as illustrated in FIG. 4. Additionally, the conversion of the amine (8) to the cis-cyclohexane derivative (9) is further treated with hydrogen bromide and ethyl acetate in propionic acid to create the hydrobromide salt of the cis-cyclohexane derivative (9). The production of the cis-cyclohexane derivative (9) is followed by epimerization of the chiral center adjacent to the ethyl ester functionality using sodium tert-butoxide to afford the trans-cyclohexane derivative (10) as a major diastereomer. After conversion to trans-cyclohexane derivative (10), the compound is subjected to reduction of the ester functionality in compound (10), using potassium borohydride in the presence of lithium chloride, to yield (1S,2S)-2-[(S)-1-phenylethyl amino]cyclohexyl)methanol (11). Generally, the conversion from compound (10) to compound (11) may incorporate tetrahydrofuran as a co-solvent and may be refluxed to afford the desired compound (11) in good overall yield.

In a further embodiment, the present invention provides commercially scalable processes for the preparation of (2S,3aR,7aS)-octahydro-1H-indole-2-carboxylic acid hydrochloride (5). Selective N-alkylation of (1S,2S)-2-[(S)-1-phenylethyl amino]cyclohexyl)methanol (11) with ethyl bromoacetate (12) was performed with sodium carbonate in acetonitrile to give compound (13). The hydroxyl functionality in compound (13) is then converted to methanesulfonate ester to afford compound (14). Subsequent treatment of compound (14) with a base, such as, but not limited to, sodium tert-butoxide in tetrahydrofuran or mixtures of tetrahydrofuran produces a trans-fused octahydroindole ring system (15) with the correct stereochemistry at the (2S)-carboxylic ester position, as the major isomer. The N-α-methylbenzyl group in (2S,3aR,7aS)-Ethyl 1-((S)-1-phenylethyl)octahydro-1H-indole-2-carboxylate (15) is cleaved by hydrogenolysis using palladium on carbon or palladium hydroxide on carbon in the presence of hydrogen and ethanol, to afford the free base form of compound (16). Thereafter, the free base form of compound (16) is subjected to acid hydrolysis by the incorporation of hydrochloric acid to provide the (2S,3aR,7aS)-octahydro-1H-indole-2-carboxylic acid (5) as its hydrochloride salt in good overall yield (See FIG. 2). Compound (5) is isolated by crystallization from acetonitrile.

In an additional embodiment, (1S,2S)-2-[(S)-1-phenylethyl amino]cyclohexyl)methanol (11) is produced from a starting material comprising ethyl 2-oxocyclohexane carboxylate (6). This embodiment comprises reacting ethyl 2-oxocyclohexane carboxylate (6) with (S)-(–)-1-phenylethylamine (7) in the presence of a catalyst, ytterbium trifluoromethanesulfonate, and heptane to produce (S)-Ethyl 2-(1-phenylethylamino)cyclohex-1-enecarboxylate (8). The next step is reduction of the amine (8) with sodium acetoxyborohydride in the presence of a acetonitrile produce (1R,2S)-Ethyl 2-((S)-1-phenylethylamino)cyclohexanecarboxylate (9), as illustrated in FIG. 1. The production of the cis-cyclohexane derivative (9) is followed by epimerization of the chiral center adjacent to the ethyl ester functionality using sodium t-butoxide to afford trans-cyclohexane derivative (10) as a major diastereomer. Reduction of the ester functionality in compound (10), using lithium borohydride yields (1S,2S)-2-[(S)-1-phenylethyl amino]cyclohexyl)methanol (11) in good overall yield, which is subsequently purified by chromatography.

In yet another embodiment, (2S,3aR,7aS)-benzyl octahydro-1H-indole-2-carboxylate hydrochloride salt (3), is produced using a starting material of crystalline ((1S,2S)-2-(S)-1-phenylethylamino)cyclohexyl)methanol (11). The first step of the process involves reaction with a catalyst including palladium on carbon in the presence of methanol to produce ((1S,2S)-2-aminocyclohexyl)methanol (17). Compound (17) is subjected to treatment with sodium cyanide in the presence of formaldehyde to produce compound (18). Subsequently, compound (18) is first reacted with trimethylsilyl chloride, and then the product of that reaction is treated with benzyl chloride to produce compound (19). Further, compound (19) is subjected to three sequential reactions to produce compound (20) as illustrated in FIG. 3. Specifically, compound (19) is first subjected to treatment with hydrochloric acid. Subsequently, methanesulfonyl chloride is added to the reaction mixture. Thereafter, potassium hydroxide is added to the reaction to produce compound (20). After compound (20) is produced, the compound is treated with aqueous mineral acid to produce the hydrochloride salt of compound (5).

BRIEF DESCRIPTION OF THE DRAWINGS

Other advantages of the present invention will be readily appreciated, as the same becomes better understood by reference to the following detailed description when considered in connection with the accompanying drawings, wherein.

DETAILED DESCRIPTION

The present invention provides for the preparation of (2S, 3aR,7aS)-octahydro-1H-indole-2-carboxylic acid hydrochloride (5) and is based on a chiral auxiliary induced diastereoselective intra-molecular ring-closure strategy. Multiple approaches may be used in the development of compound (5), all of which are encompassed by the current invention. Specifically, one approach may incorporate the use of a catalyst, whereas another embodiment may rely on an acid solvent to produce the compound. In one embodiment of the present invention, the auxiliary employed is (S)-(−)-1-phenylethylamine (7) in the presence of a catalyst. This allows setting of the trans-fused absolute chirality in octahydroindole bicyclic ring system based upon modification of the literature as described in FIG. 1 [See Cimarelli et al., *Tetrahedon Asymmetry* 1994, 5, 1455 and *J. Am. Chem. Soc.* 1996, 118, 5502], but more importantly, it allows introduction of correct stereochemistry at the (2S)-carboxylic acid position as described in FIG. 2. In another embodiment of the present invention, the auxiliary employed is (S)-(−)-1-phenylethylamine (7) in the presence of a solvent, without incorporating a catalyst based upon modification of the literature as described in FIG. 4 [See Xu D et al., *Tetrahedron Asymmetry*, Vol. 8, No. 9, pp/1445-51, 1997].

1. Catalyst Approach

Figure 1:
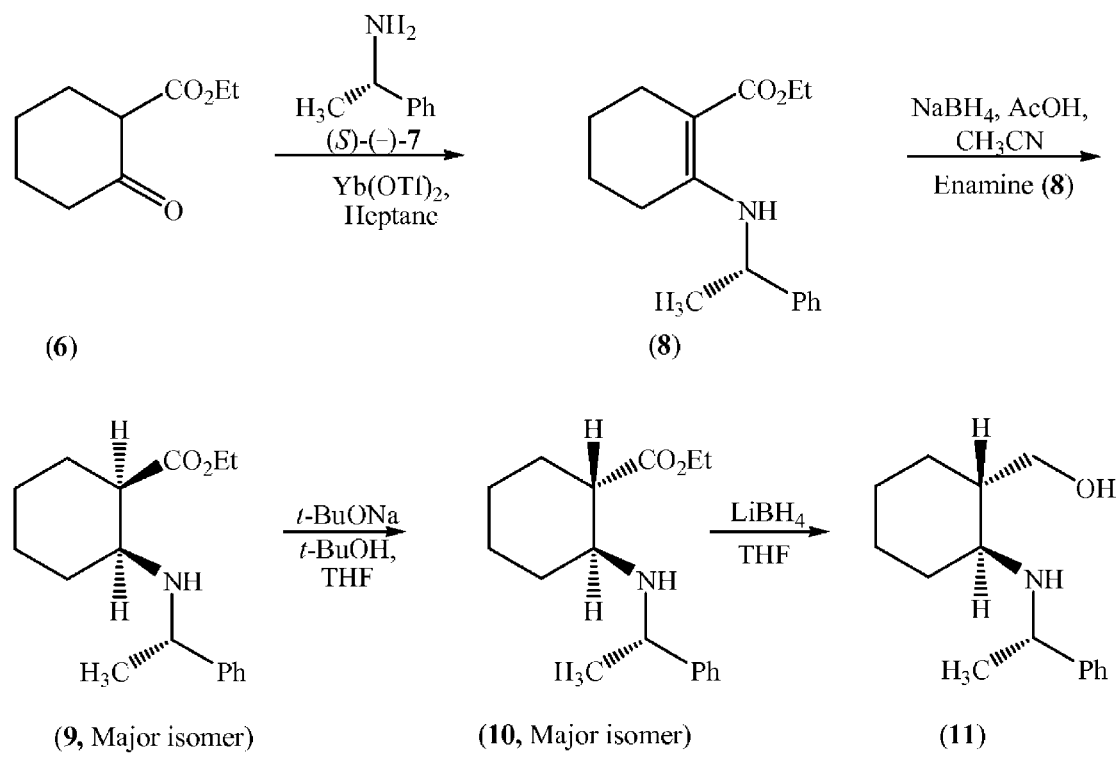
FIG. 1 illustrates a process for making (1S,2S)-2-[(S)-1-phenylethyl amino]cyclohexyl)methanol (11), comprising the use of ytterbium trifluoromethanesulfonate as a catalyst.

In one embodiment, the process of the present invention may utilize ethyl 2-oxocyclohexane carboxylate (6) to prepare (1S,2S)-2-[(S)-1-phenylethyl amino]cyclohexyl)methanol (11) as described in FIG. 1 by modification of synthesis methods found in the literature [*Tetrahedon Asymmetry* 1994, 5, 1455 and *J. Am. Chem. Soc.* 1996, 118, 5502]. Thus, ethyl 2-oxocyclohexane carboxylate (6) may be treated with (S)-(−)-1-phenylethylamine (7) in the presence of a Lewis acid catalyst in aprotic solvents including, but not limited to, heptanes, or toluene, produced (S)-Ethyl 2-(1-phenylethylamino)cyclohex-1-enecarboxylate (8). As described in Hayashi et al., *J. Am. Chem. Soc.*, 1996, 118, 5502-03, the catalyst may be ytterbium trifluoromethanesulfonate [Yb (CF$_3$SO$_3$)$_3$, also known as Yb(OTf)$_3$]. Reduction of the amine (8) with selective reducing agents, such as, but not limited to, sodium acetoxyborohydride or N-Selectride in the presence of a co-solvent, may be used to produce (1R,2S)-Ethyl 2-((S)-1-phenylethylamino)cyclohexanecarboxylate (9), as illustrated in FIG. 1. The production of the cis-cyclohexane derivative (9) is followed by epimerization of the chiral center adjacent to the ethyl ester functionality using a base, including, but not limited to, sodium t-butoxide or lithium hexamethyldisilazide, affording the trans-cyclohexane derivative (10) as a major diastereomer. Reduction of the ester functionality in compound (10), using reagents such as, but not limited to, lithium borohydride or potassium borohydride, yielded (1S,2S)-2-[(S)-1-phenylethyl amino]cyclohexyl)methanol (11) in good overall yield, which may be purified by chromatography and isolated as a crystalline solid. Given the inexpensive and readily available starting materials, the process described herein for the development of (1S,2S)-2-[(S)-1-phenylethyl amino]cyclohexyl)methanol (11) is considered a desirable alternative.

2. Solvent Approach

Figure 4:
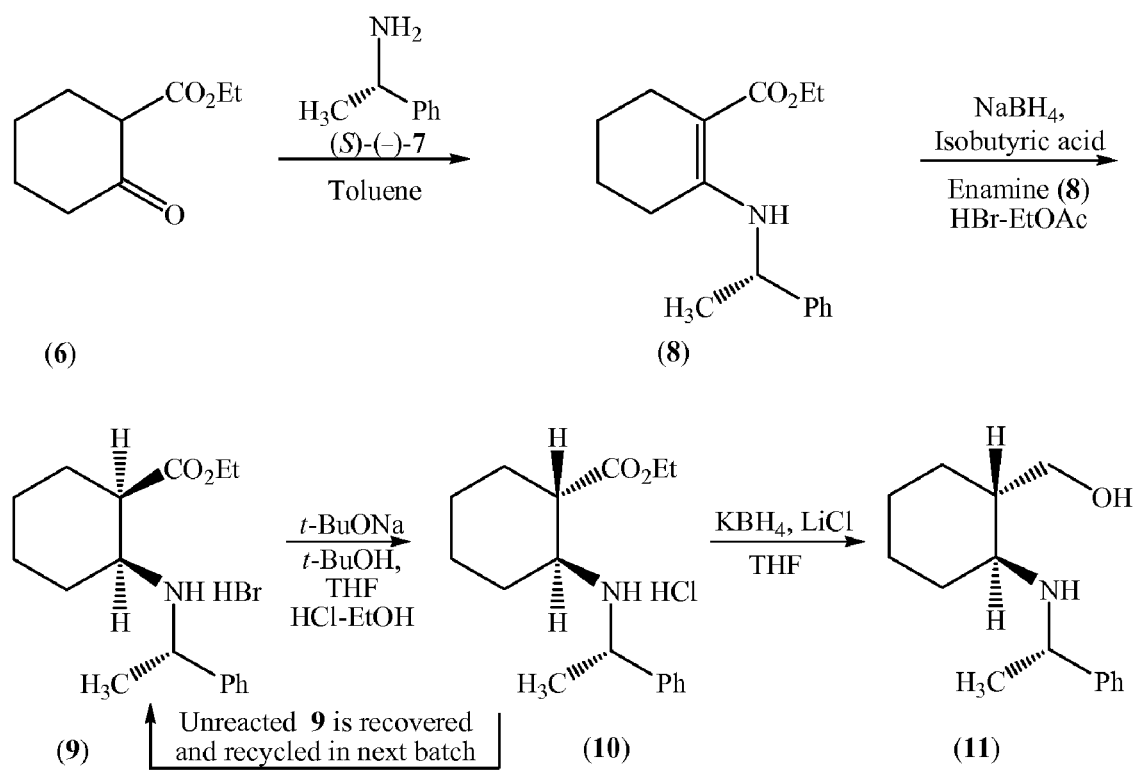
FIG. 4 illustrates a process for making (1S,2S)-2-[(S)-1-phenylethyl amino]cyclohexyl)methanol (11), comprising the use of toluene as a solvent, without the incorporation of a catalyst.

In another embodiment, the present invention may utilize ethyl 2-oxocyclohexane carboxylate (6) to prepare (1S,2S)-2-[(S)-1-phenylethyl amino]cyclohexyl)methanol (11) as described in FIG. 4 by modification of methods of synthesis using an aprotic solvent to produce an amine [See Xu D et al., *Tetrahedron Asymmetry*, Vol. 8, No. 9, pp/1445-51, 1997]. The current embodiment may comprise reacting ethyl 2-oxocyclohexane carboxylate (6) with (S)-(−)-1-phenylethylamine (7) in the presence of an aprotic solvent including, but not limited to, toluene and acetonitrile, to produce (S)-Ethyl 241-phenylethylamino)cyclohex-1-enecarboxylate (8). The ratio of compound (6) to compound (7) generally ranges from approximately 10:1 to approximately 1:10. In one embodiment, the ratio of compound (6) to compound (7) ranges from approximately 5:1 to approximately 1:5. In another embodiment, the ratio of compound (6) to compound (7) ranges from approximately 2:1 to approximately 1:2. In an additional embodiment, the ratio of compound (6) to compound (7) comprises approximately 1:1.05.

The modification encompassed within the current embodiment provides unique benefits not experienced with the methods incorporating a Lewis acid catalyst such as ytterbium trifluoromethanesulfonate [Yb(CF$_3$SO$_3$)$_3$, also known as Yb(OTf)$_3$], as previously discussed. The current embodiment eliminates the need for the incorporation of a Lewis acid catalyst Yb(OTf)$_3$. Due to the fact that ytterbium compounds are known to be toxic, the elimination of this catalyst from the current embodiment provides an improved safety profile for the process, as well as a more cost-effective alternative to other methods.

Further, reduction of the amine (8) with selective reducing agents, such as, but not limited to, sodium borohydride or N-Selectride in the presence of an acid and a co-solvent, can be used to produce (1R,2S)-Ethyl 2-((S)-1-phenylethylamino)cyclohexanecarboxylate (9), as illustrated in FIG. 4. The acid may include, but is not limited to, acetic acid, isobutyric acid, pivalic acid, benzoic acid, trifluouroacetic acid, and phenylacetic acid. The acid is generally added to the reaction at a temperature ranging from approximately −20° C. to approximately 40° C., and in another embodiment, the reaction temperature ranges from approximately 0° C. to approximately 20° C. Additionally, the co-solvent may include, but is not limited to, toluene and acetonitrile. The co-solvent is generally maintained at a temperature ranging from approximately −10° C. to approximately 10° C., and in another embodiment, the reaction temperature ranges from approximately −2° C. to approximately 2° C. Further, the addition of a co-solvent to the reaction may be accompanied by the addition of a base, including, but not limited to, sodium hydroxide, to increase the pH of the reaction to a pH in the range of approximately 8 to approximately 10. In another embodiment, the base is added to achieve a pH of approximately 9.

One skilled in the art will appreciate that the cis-cyclohexane derivative (9) may be produced by the incorporation of any of the acids and co-solvents described herein, in an acceptable yield. However, use of the combination of toluene as a co-solvent with isobutyric acid offered similar yields and an improved cis/trans ratio compared to pivalic acid, while also providing easier handling with isobutyric acid compared to pivalic acid. Therefore, the embodiment illustrated in FIG. 4 provides additional benefits due to the fact that the toluene used in the conversion of ethyl 2-oxocyclohexane carboxylate (6) to the amine (8) provides the necessary co-solvent needed in combination with isobutyric acid to convert the amine (8) to the cis-cyclohexane derivative (9). The ability to use the same solvent in the conversion from compound (6) to compound (8) and the conversion of compound (8) to compound (9) provides for greater efficiencies, decreasing the number of solvents required and providing a more cost-effective alternative.

The conversion of the amine (8) to the cis-cyclohexane derivative (9) may be performed with excellent yield and optical purity if the reaction is further treated with hydrogen bromide and ethyl acetate in propionic acid to create the hydrobromide salt of the cis-cyclohexane derivative (9). It is further contemplated that the treatment of the cis-cyclohexane derivative may be performed in the presence of hydrogen bromide gas as well. The production of compound (9) results in a diastereomeric excess/enantiomeric excess (de/ee) of approximately 85% or greater. In one embodiment, the diastereomeric excess/enantiomeric excess of the cis-cyclohexane derivative comprises approximately 95% or greater. It was also discovered that further treatment of cis-cyclohexane derivative (9) with acetonitrile may increase the diastereomeric excess/enantiomeric excess to approximately 99% or greater. Additionally, after treatment with acetonitrile, the overall yield of cis-cyclohexane derivative (9) ranges from approximately 75% to approximately 85%. The treatment with acetonitrile is generally conducted at a temperature ranging from approximately −10° C. to approximately 0° C. In an additional embodiment, the temperature ranges from approximately −2° C. to approximately 2° C. As such, the current invention is a modification of the teachings of Xu et al., as it relates to the conversion of the amine (8) to the cis-cyclohexane derivative (9).

The conversion of the amine (8) to the cis-cyclohexane derivative (9) as disclosed in the current embodiment, provides benefits not previously experienced. The previous embodiment disclosed the use of sodium acetoxyborohydride in the presence of acetic acid and acetonitrile to convert the amine (8) to (1R,2S)-Ethyl 2-((S)-1-phenylethylamino) cyclohexanecarboxylate (9). The previous embodiment is a modification and improvement of the method as taught by Cimarelli et al., *Tetrahedron Asymmetry*, Vol. 5, No. 8, pp. 1455-1458, 1994]. Although the method of the previous embodiment may be used to produce the cis-cyclohexane derivative (9), as depicted in FIG. 1, the previous embodiment is limited in the fact that it may require chromatographic purification to isolate the desired diastereomer, as previously discussed. The process of chromatographic purification is inefficient, especially as applied to production scale activities. Therefore, the modifications and improvements incorporated in the conversion of the amine (8) to the cis-cyclohexane derivative (9) as illustrated in FIG. 4 provide substantial efficiency benefits by not requiring chromatographic purification.

As an alternative approach for the conversion of compound (8) to compound (9), the use of a hydrogenation step may be utilized. The inventors of the current invention have also found that modification of the processes described in WO 2009/015166 to Santella et al., which is fully incorporated herein by reference, may be used for the conversion from compound (8) to cis-cyclohexane derivative (9). Specifically, rather than the use of an acid such as isobutyric acid in the presence of an acid, compound (8) may be subjected to catalytic hydrogenation to produce compound. The catalytic hydrogenation may generally include the incorporation of a catalyst including, but not limited to, carbon supported nanoparticles (Pt/C), and the use of a hydrogenating agent including, but not limited to, acetic acid. The conversion of compound (8) to compound (9) may also incorporate the use of an additional compound, comprising ethanol to further support the hydrogenation of compound (8). The hydrogenation reaction yields the major aminoester diastereomer, with only a small amount of the minor aminoester diastereomer. The hydrogenation reaction described herein may provide advantages in the form of better stereoselectivity and greater cost effectiveness.

The production of the cis-cyclohexane derivative (9) is followed by epimerization of the chiral center adjacent to the ethyl ester functionality using a base, including, but not limited to, sodium tert-butoxide or lithium hexamethyldisilazide, to afford the trans-cyclohexane derivative (10) as a major diastereomer. The epimerization reaction is typically performed in the presence of one or more additional compounds including, but not limited to, tetrahydrofuran and tert-butanol. Generally, the conversion from compound (9) to compound (10) is performed at a temperature ranging from approximately −5° C. to approximately 35° C. In one embodiment, the temperature is in the range of approximately 6° C. to approximately 25° C. The conversion of cis-cyclohexane derivative (9) to the trans-cyclohexane derivative (10) generally results in a yield of the trans-isomer of approximately 75% to approximately 85%, while the remaining approximately 15% to approximately 25% comprises the cis-isomer. It should be noted that the hydrobromide salt of cis-cyclohexane derivative (9) may also be converted to the free base form of the compound prior to converting to compound (10) by reacting the compound with sodium carbonate and heptane.

The current embodiment has modified and improved the teachings of the prior art, as disclosed in Hayashi et al., *J. Am. Chem. Soc.*, 1996, 118, 5502-03, by additionally incorporating a recapture and recycling step, such that the portion of cis-cyclohexane derivative (9) that is not converted into trans-cyclohexane derivative (10) may be recaptured and re-inserted into the reaction to further increase the yield of the trans-isomer, as illustrated in FIG. 4. The recycling of the unreacted cis-cyclohexane derivative (9) generally incorporates the use of hydrogen chloride in ethanol to transform the trans-cyclohexane derivative (10) and cis-cyclohexane derivative (9) into the hydrochloride salt of trans-cyclohexane derivative (10), with a yield of approximately 60% to approximately 70%, and a stereoselectivity of approximately 99% or greater of the trans-isomer. With the incorporation of the recapture and recycling process, the yield of the trans-cyclohexane derivative (10) may be increased to approximately 99% or greater. The Hayashi reference does not teach that the cis-cyclohexane derivative (9) remaining after the partial conversion to trans-cyclohexane derivative (10) may be recycled and reintroduced into the reaction. Therefore, the yields achieved with the current method are significantly greater than those attained according to the Hayashi method, and the current embodiment is an improvement over the prior art.

After conversion to trans-cyclohexane derivative (10), the compound is subjected to reduction of the ester functionality in compound (10), using reagents such as, but not limited to, potassium borohydride in the presence of lithium chloride, to yield (1S,2S)-2-[(S)-1-phenylethyl amino]cyclohexyl)methanol (11). Generally, the conversion from compound (10) to compound (11) may incorporate tetrahydrofuran as a co-solvent and may be refluxed to afford the desired compound (11) in good overall yield. It should be noted that compound (10) may be converted to the free base from the hydrochloride salt by reaction with sodium carbonate prior to conversion to compound (11).

The conversion from trans-cyclohexane derivative (10) to (1S,2S)-2-[(S)-1-phenylethyl amino]cyclohexyl)methanol (11) is a modification and improvement over prior art methods as disclosed in Schinnerl et al., *Eur. J. Org. Chem.*, 2003, 721-726. The current embodiment incorporates the use of potassium borohydride in the presence of lithium chloride, rather than lithium borohydride. The inventors surprisingly found that the overall yield of compound (11) was similar to previous methods; however, the use of potassium borohydride provides substantial cost savings, resulting in greater cost-effectiveness of the method.

3. Process for Generating (2S,3aR,7aS)-octahydro-1H-indole-2-carboxylic acid (5)

a. Under the Catalyst Approach

Figure 2:
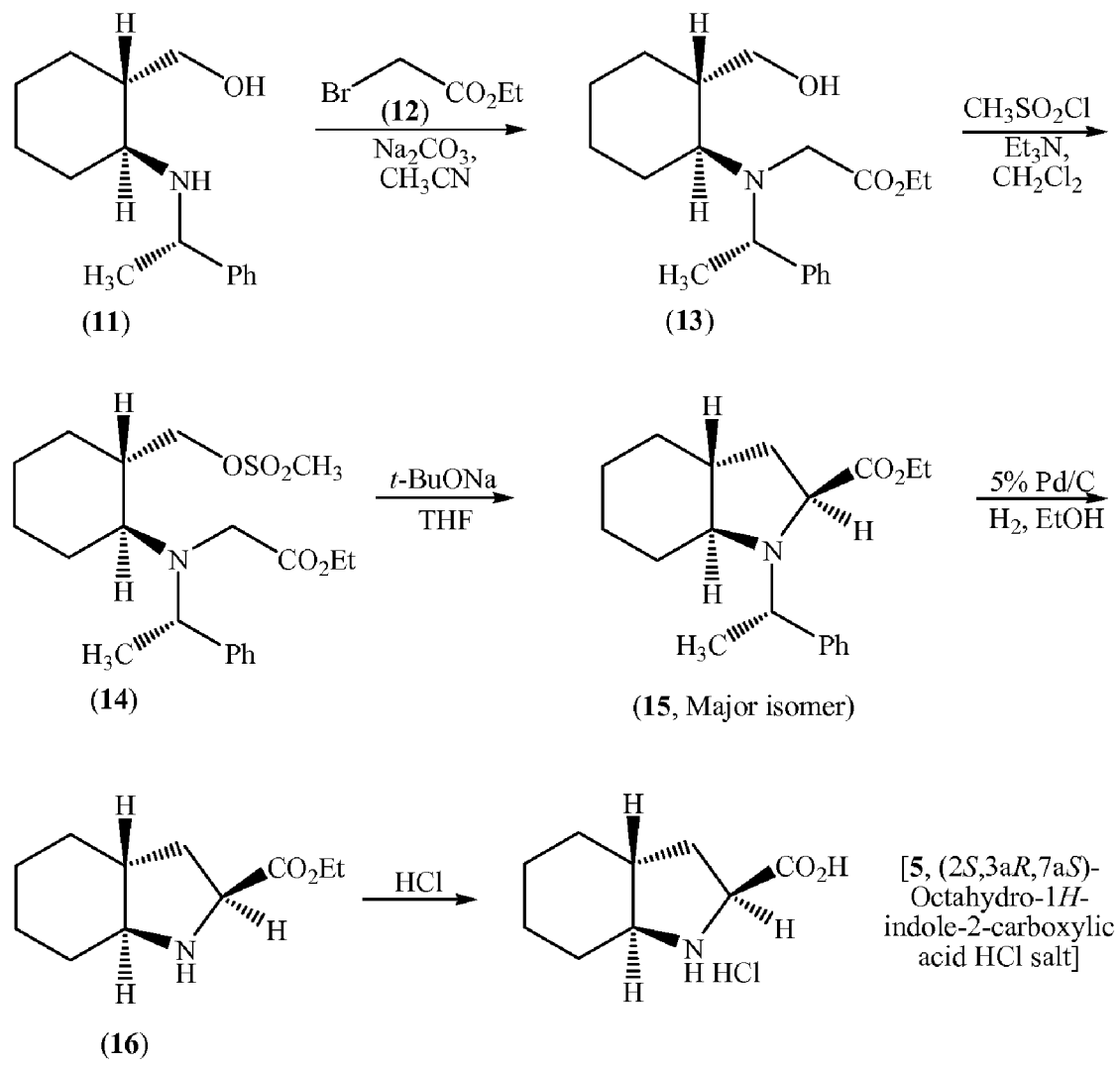
FIG. 2 illustrates a first process for making (2S,3aR,7aS)-octahydro-1H-indole-2-carboxylic acid (5), wherein intermediate compound (16) comprises the free base form of the compound.

The (1S,2S)-2-[(S)-1-phenylethyl amino]cyclohexyl)methanol (11) compound produced by the steps previously described under the catalyst approach may further be incorporated into the process illustrated in FIG. 2. Selective N-alkylation of (1S,2S)-2-[(S)-1-phenylethyl amino]cyclohexyl)methanol (11) with ethyl bromoacetate (12) was performed with a base such as, but not limited to, sodium carbonate, sodium bicarbonate, or potassium carbonate, in acetonitrile or tetrahydrofuran to give compound (13). The hydroxyl functionality in compound (13) was converted to a leaving group, such as, but not limited to, methanesulfonate ester, trifluoromethane sulfonate ester, chloride, bromide, or iodide, to afford compound (14). The conversion to a leaving group may be reacted in the presence of triethylamine and dichloromethane.

It should be noted that compound (14) as illustrated in FIG. 2 comprises the resulting compound when the hydroxyl functional group of compound (13) is converted to a methanesulfonate ester. However, compound (14) may exist in alternative embodiments without departing from the scope of the current invention. Specifically, compound (14) may exist according to following structure:

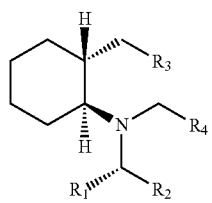

wherein R1 and R2 are each selected from the group consisting of alkyl, alkenyl, alkynyl, aryl, heteroaryl, cycloalkyl, alkylsulfinyl, and arylsulfinyl, each of which is substituted with aryl, heteroaryl, or cycloalkyl; R3 is a suitable leaving group selected from the group consisting of mesylate, triflate, tosylate, methanesulfonate ester, trifluoromethane sulfonate ester, chloride, bromide, and iodide; and R4 is selected from the group consisting of ester, nitrile, alkenyl, alkynyl, sulfonyl, aryl, and heteroaryl.

Treatment of compound (14) with a base, such as, but not limited to, sodium tert-butoxide, sodium hydride, or lithium diisopropylamide, in solvents, such as, but not limited to, tetrahydrofuran or mixtures of tetrahydrofuran and heptanes, produced a trans-fused octahydroindole ring system (15) with the correct stereochemistry at the (2S)-carboxylic ester position, as the major isomer. Generally, in order for the reaction to proceed with acceptable yields, compound (15) may be purified by column chromatography prior to any further processing. The N-α-methylbenzyl group in (2S,3aR,7aS)-Ethyl 1-((S)-1-phenylethyl)octahydro-1H-indole-2-carboxylate (15) is cleaved by hydrogenolysis using metal catalysts, such as, but not limited to, palladium on carbon or palladium hydroxide on carbon, in the presence of hydrogen gas and ethanol to afford compound (16). Subsequently, compound (16) was subjected to acid hydrolysis to provide the (2S,3aR,7aS)-octahydro-1H-indole-2-carboxylic acid (5) as its hydrochloride salt in good overall yield.

b. Under the Solvent Approach

Figure 5:
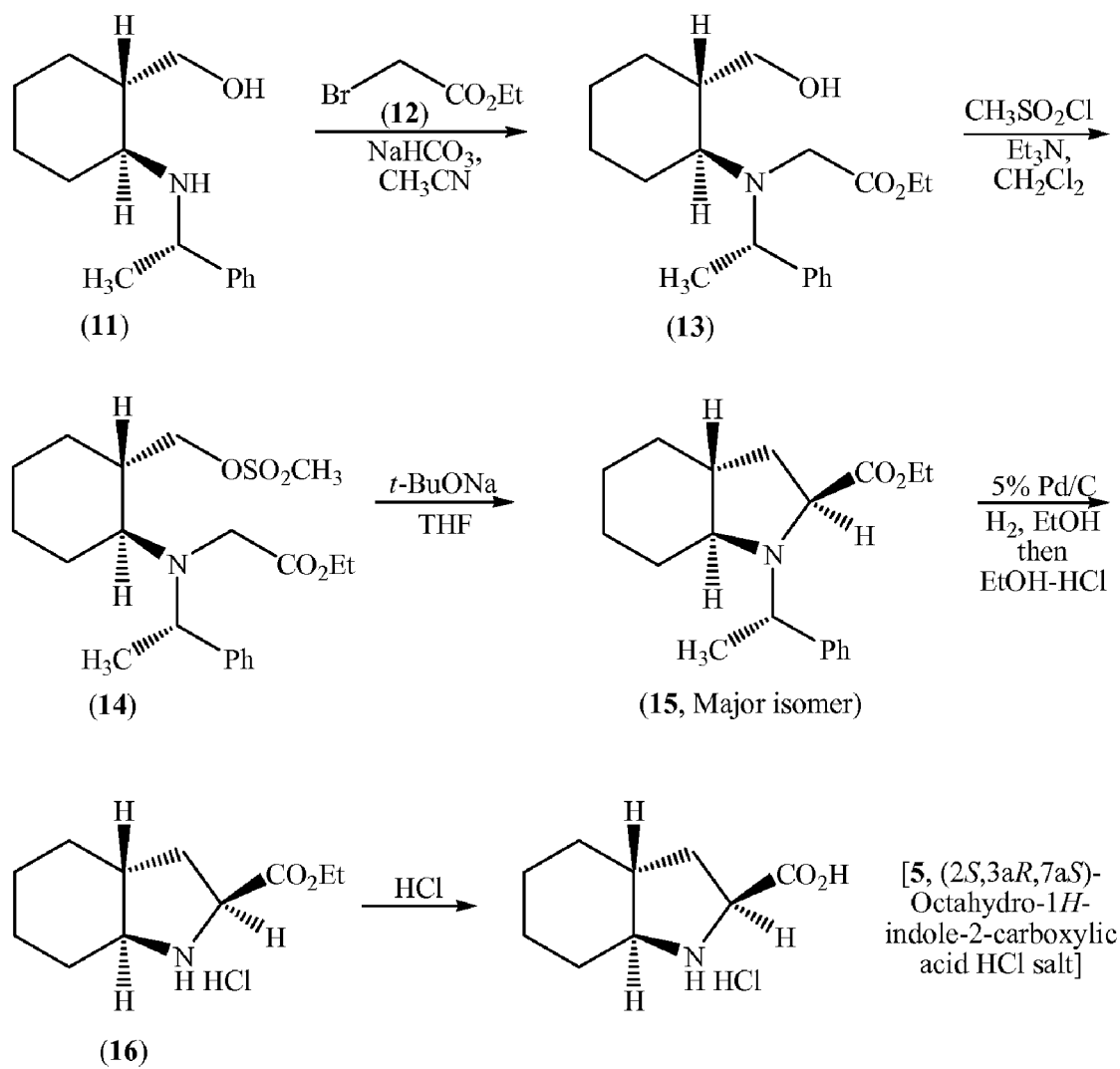
FIG. 5 illustrates the process for making (2S,3aR,7aS)-octahydro-1H-indole-2-carboxylic acid (5) wherein intermediate compound (16) comprises the hydrochloride salt form of the compound.

The current embodiment also encompasses a new process for the development of (2S,3aR,7aS)-octahydro-1H-indole-2-carboxylic acid (5), using the starting material (1S,2S)-2-[(S)-1-phenylethyl amino]cyclohexyl)methanol (11) produced in the previous steps under the solvent approach, as illustrated in FIG. 5. Selective N-alkylation of (1S,2S)-2-[(S)-1-phenylethyl amino]cyclohexyl)methanol (11) with ethyl bromoacetate (12) was performed with a base such as, but not limited to, sodium bicarbonate, sodium carbonate, or potassium carbonate, in acetonitrile to give compound (13). It should be noted that it is also possible to incorporate ethyl chloroacetate instead of ethyl bromoacetate (12) without departing from the scope of the current invention. The hydroxyl functionality in compound (13) was converted to a leaving group, such as, but not limited to, methanesulfonate ester, trifluoromethane sulfonate ester, chloride, bromide, or iodide, to afford compound (14). The conversion to a leaving group may be reacted in the presence of triethylamine and dichloromethane. The conversion from compound (13) to compound (14) generally incorporates a temperature ranging from approximately −10° C. to approximately 20° C. In another embodiment, the conversion of compound (13) to compound (14) is performed at a temperature ranging from approximately 0° C. to approximately 10° C. Further, the reaction is allowed to proceed for a sufficient amount of time, generally not less than one hour.

It should be noted that compound (14) as illustrated in FIG. 4 comprises the resulting compound when the hydroxyl functional group of compound (13) is converted to a methanesulfonate ester. However, compound (14) may exist in alternative embodiments without departing from the scope of the current invention. Specifically, compound (14) may exist according to following structure:

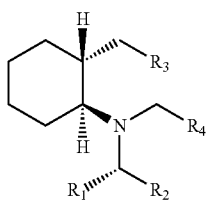

wherein R1 and R2 are each selected from the group consisting of alkyl, alkenyl, alkynyl, aryl, heteroaryl, cycloalkyl, alkylsulfinyl, and arylsulfinyl, each of which is substituted with aryl, heteroaryl, or cycloalkyl; R3 is a suitable leaving group selected from the group consisting of mesylate, triflate, tosylate, methanesulfonate ester, trifluoromethane sulfonate ester, chloride, bromide, and iodide; and R4 is selected from the group consisting of ester, nitrile, alkenyl, alkynyl, sulfonyl, aryl, and heteroaryl.

Treatment of compound (14) with a base, such as, but not limited to, sodium tert-butoxide, sodium hydride, or lithium diisopropylamide, in solvents, such as, but not limited to, tetrahydrofuran or mixtures of tetrahydrofuran and heptanes, produced a trans-fused octahydroindole ring system (15) with the correct stereochemistry at the (2S)-carboxylic ester position, as the major isomer. The yield of (2S)-isomer for compound (15) generally ranges from about 90% to about 99%, and the yield of (2R)-isomer generally ranges from about 1% to about 10%. In another embodiment, the ratio of (2S)-isomer to (2R)-isomer of compound (15) is approximately 95:5. Additionally, the conversion of compound (14) is generally performed at a temperature ranging from approximately 20° C. to approximately 65° C., and the reaction is allowed to proceed for a sufficient amount of time, generally not less than one hour.

Compared to prior art methods and the previous embodiments described herein, the production of compound (15) according to this embodiment does not require purification by chromatography, thus providing significant benefits over previous methods. The N-α-methylbenzyl group in (2S,3aR, 7aS)-Ethyl 1-((S)-1-phenylethyl)octahydro-1H-indole-2-carboxylate (15) is cleaved by hydrogenolysis using metal catalysts, such as, but not limited to, palladium on carbon or palladium hydroxide on carbon in the presence of hydrogen gas, ethanol, and hydrogen chloride, to afford the hydrochloride salt of compound (16). The overall yield of compound (16) ranges from approximately 35% to approximately 45%, after a five-step process wherein compound (10) is used as the starting material. Incorporating compound (6) as the starting material, and using the solvent approach as described herein, the yield of compound (16) ranges from approximately 15% to approximately 25%, after an eight-step process.

Thereafter, the hydrochloride salt of compound (16) is subjected to acid hydrolysis by the incorporation of an acid including, but not limited to, 6 N hydrochloric acid to provide the (2S,3aR,7aS)-octahydro-1H-indole-2-carboxylic acid (5) as its hydrochloride salt in good overall yield (See FIG. 5). It should be noted that compound (5) is isolated by crystallization from a solvent including, but not limited to, acetonitrile. Additionally, the yield of the hydrochloride salt of compound (5) compared to the amount of compound (16) ranges from approximately 80% to approximately 90%.

Subsequently, crystallized compound (5) may be subjected to esterification to produce (2S,3aR,7aS)-benzyl octahydro-1H-indole-2-carboxylate hydrochloride salt (3), a key intermediate in the production of trandolaprilat and trandolapril. This step final step is known within the art, and generally comprises treatment with esterification agents including, but not limited to, thionyl chloride, benzyl alcohol, and dichloromethane, as disclosed in U.S. Pat. No. 4,879,392. Although the conversion of compound (5) to compound (3) is disclosed, the processes for the production of compound (5), as detailed herein are novel and convey significant improvements over the prior art.

Alternatively, it is also possible to convert the hydrochloride salt of (2S,3aR,7aS)-Ethyl 1-((S)-1-phenylethyl)octahydro-1H-indole-2-carboxylate (16) directly into (2S,3aR, 7aS)-benzyl octahydro-1H-indole-2-carboxylate hydrochloride salt (3) without converting compound (16) to compound (5). This process involves the reaction of compound (16) with benzyl alcohol in the presence of heat, and the removal of ethanol.

The cumulative process described in the two previous embodiments for the production of (2S,3aR,7aS)-octahydro-1H-indole-2-carboxylic acid (5) from ethyl 2-oxocyclohexane carboxylate (6) provides multiple advantages over the prior act methods. Primarily, the embodiments provide a nine-step process for the production of compound (5), which is useful in the production of clinically significant compounds, such as trandolapril, described previously. The reduction in the number of steps provides significant benefits with regard to the efficiencies of production, as well as improving the cost-effectiveness of the production. Additionally, the process requires less solvent compared to previous methods, thereby providing additional cost benefits.

Figure 3:
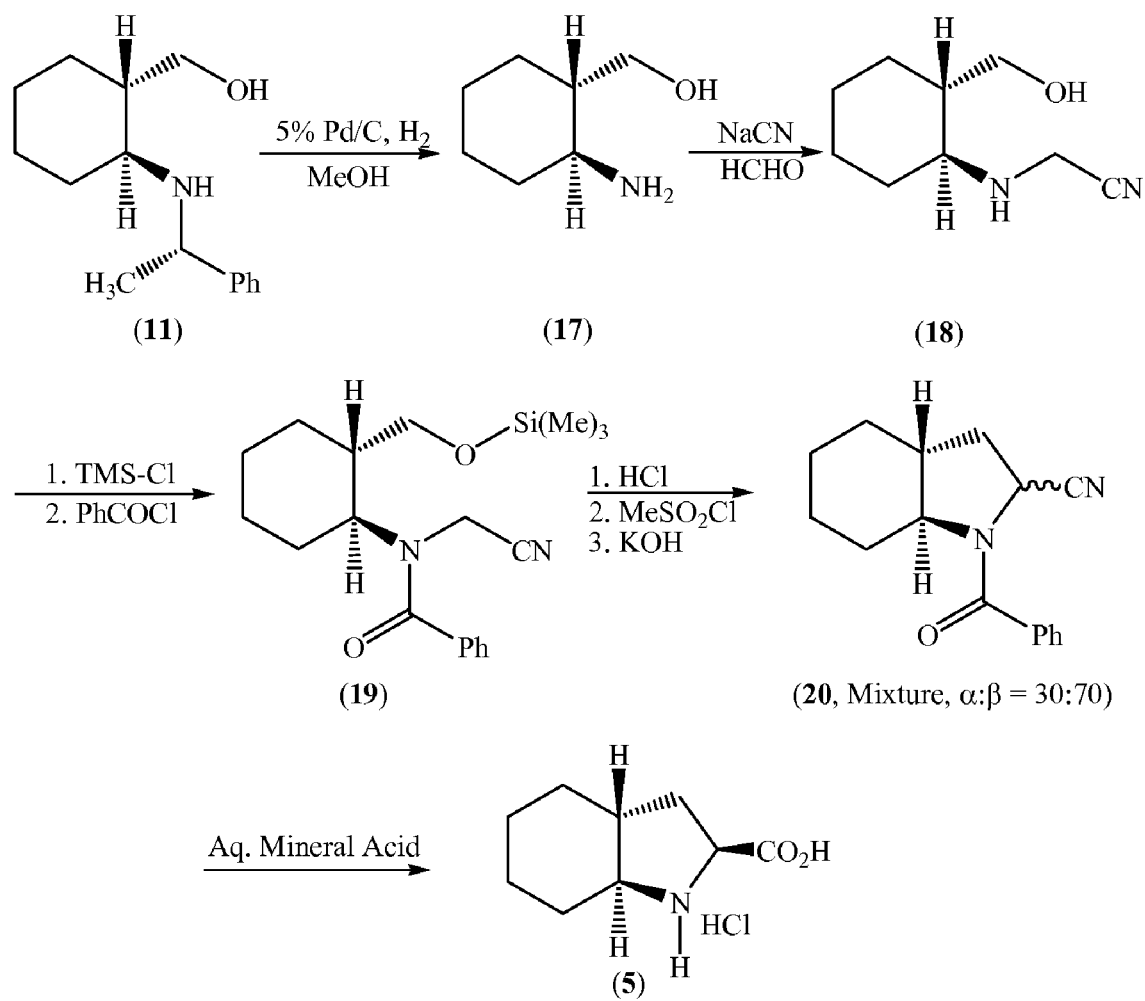
FIG. 3 illustrates the process for making (2S,3aR,7aS)-octahydro-1H-indole-2-carboxylic acid (5) by using (1S,2S)-2-[(S)-1-phenylethyl amino]cyclohexyl)methanol (11) as a starting material.

4. Alternative Process for Generating (2S,3aR,7aS)-octahydro-1H-indole-2-carboxylic acid (5) Using the Hoffman Reaction Additionally, as depicted in FIG. 3, the production of (2S, 3aR,7aS)-benzyl octahydro-1H-indole-2-carboxylate hydrochloride salt (3), a key intermediate in the production of trandolaprilat and trandolapril, may be produced using a starting material of crystalline ((1S,2S)-2-((S)-1-phenylethylamino)cyclohexyl)methanol (11). The first step of the process involves reaction with a catalyst including, but not limited to, palladium on carbon or palladium hydroxide on carbon in the presence of an alcohol such as methanol to produce ((1S,2S)-2-aminocyclohexyl)methanol (17). The remaining steps in the conversion of compound (17) to the hydrochloride salt, and eventual conversion to (2S,3aR,7aS)-benzyl octahydro-1H-indole-2-carboxylate hydrochloride salt (3) are based upon the teachings of U.S. Pat. No. 4,879, 392, which is fully incorporated herein by reference. Generally, the remaining steps can be described as follows. Compound (17) is subjected to treatment with sodium cyanide in the presence of formaldehyde to produce compound (18), as illustrated in FIG. 3. Subsequently, compound (18) is first reacted with trimethylsilyl chloride, and then the product of that reaction is treated with benzyl chloride to produce compound (19). Further, compound (19) is then subjected to three sequential reactions to produce compound (20) as illustrated in FIG. 3. Specifically, compound (19) is first subjected to treatment with hydrochloric acid. Subsequently, methanesulfonyl chloride is added to the reaction mixture. Thereafter, potassium hydroxide is added to the reaction to produce compound (20). After compound (20) is produced, the compound is treated with aqueous mineral acid to produce the hydrochloride salt of compound (5), as disclosed previously. As described previously, compound (5) may then be treated with thionyl chloride, benzyl alcohol, and dichloromethane to produce (2S,3aR,7aS)-benzyl octahydro-1H-indole-2-carboxylate hydrochloride salt (3).

5. The Current Embodiments Compared to Previous Methods

Figure 6:
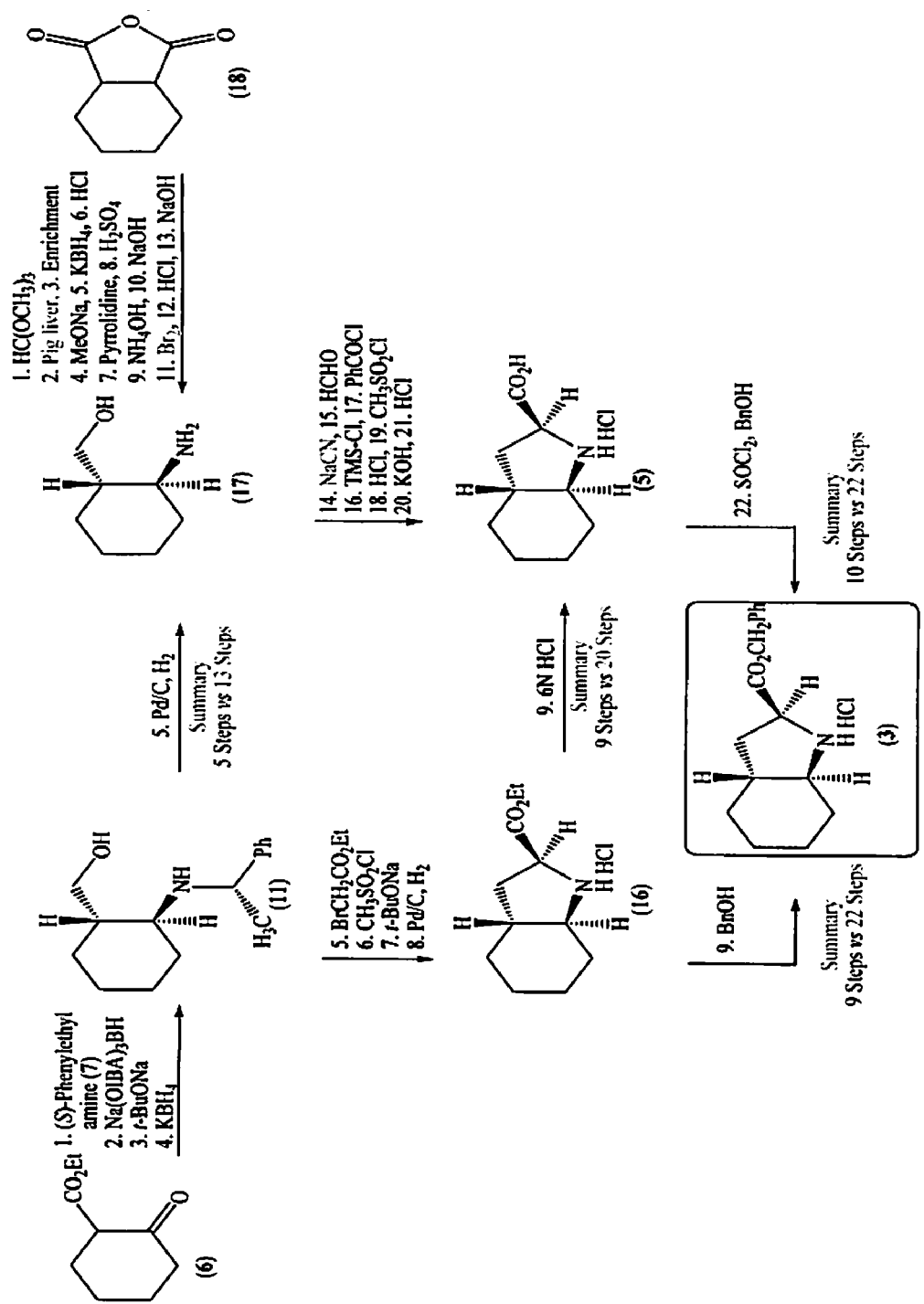
FIG. 6 depicts a chart showing the various embodiments of the current invention and how they compare to methods of producing (2S,3aR,7aS)-benzyl octahydro-1H-indole-2-carboxylate hydrochloride salt (3) disclosed in the prior art. Specifically, FIG. 6 outlines the differences between the current methods and previous methods by depicting the reduction in total steps required for production of compound (3) in all embodiments and the efficiencies gained from the reduction of steps.

FIG. 6 illustrates the differences between the embodiments discussed herein and other embodiments. The ultimate goal of the current invention is to produce (2S,3aR,7aS)-benzyl octahydro-1H-indole-2-carboxylate hydrochloride salt (3), which is a key intermediate compound in the production of trandolaprilat and trandolapril. According to previous methods, the production of compound (3) requires a process that entails twenty-two steps and a cycle time of 11-12 weeks. The current invention reduces the number of steps in the process by the several embodiments described herein. In one embodiment, under the solvent approach, the current invention describes a four-step process to produce compound (11) from a starting material of ethyl 2-oxocyclohexane carboxylate (6) (a keto-ester) as shown in FIG. 6. The production of compound (11) can then be followed by a five step process to produce compound (5), and the one-step conversion of compound (5) to compound (3), which was previously disclosed in the art. Thus, under the solvent approach, a keto-ester can be converted into compound (3) in ten steps, as opposed to the twenty-two steps described in the prior art. Furthermore, the cycle time for the solvent approach is only 3-4 weeks. In addition, the solvent approach does not require a catalyst and requires less solvent than other methods, leading to a more efficient and cost-effective alternative with a significantly decreased cycle time.

In another embodiment, similarly incorporating the solvent approach, as illustrated in FIG. 6, compound (11) can be produced in four steps, and compound (16) may be produced in an additional four steps. However, in this embodiment compound (16) may be directly converted into compound (3), without the conversion to compound (5). In this embodiment, the conversion from the keto-ester to compound (3) includes a total of nine steps, as opposed to twenty-two steps, with all of the benefits previously described. Therefore, this embodiment provides numerous advantages compared to previous methods.

In a further embodiment, illustrated in FIG. 6, ethyl 2-oxocyclohexane carboxylate (6) may be converted to compound (11) by means of the catalyst approach, as described herein, which also requires a four-step process. In this embodiment, the production of compound (11) can then be followed by a five step process to produce compound (5), and the one-step conversion of compound (5) to compound (3), which was previously disclosed in the art. Thus, under the solvent approach, a keto-ester can be converted into compound (3) in ten steps, as opposed to the twenty-two steps described in the prior art. Thus, the method of this embodiment requires significantly fewer steps, leading to a more efficient and cost-effective alternative.

In yet another embodiment, illustrated in FIG. 6, ethyl 2-oxocyclohexane carboxylate (6) may be converted to compound (11) by means of the catalyst approach, as described herein, which also requires a four-step process. Similar to the previous embodiments, compound (16) may be produced in an additional four steps. However, in this embodiment compound (16) may be directly converted into compound (3), without the conversion to compound (5). In this embodiment, the conversion from the keto-ester to compound (3) includes a total of nine steps, as opposed to twenty-two, with all of the benefits previously described. Therefore, this embodiment provides numerous advantages including fewer steps, leading to a more efficient and cost-effective alternative.

In an additional embodiment, illustrated in FIG. 6, compound (11) may be converted into ((1S,2S)-2-aminocyclohexyl)methanol (17). Compound (17) can then be subsequently converted into compound (5) by means of eight intermediate steps, as described in U.S. Pat. No. 4,879,392. As described previously, compound (5) can then undergo a one-step conversion to produce (2S,3aR,7aS)-benzyl octahydro-1H-indole-2-carboxylate hydrochloride salt (3). Therefore, the conversion of compound (11) to compound (3) requires 10 steps, rather than the twenty-two steps described by the prior art process. Regardless of whether the solvent approach or the catalyst approach is used to produce compound (11), both approaches require four steps to convert the keto-ester starting material into compound (11). Therefore, under this embodiment, to convert the keto-ester starting material [compound (6)] into compound (3) requires a total of fourteen steps, compared to the twenty-two step process of other methods. Accordingly, this embodiment requires fewer steps, leading to a more efficient and cost-effective process for producing compound (3).

The compounds and processes of the invention will be better understood by reference to the following examples, which are intended as an illustration of and not a limitation upon the scope of the invention. Each example illustrates at least one method of preparing various intermediate compounds and further illustrates each intermediate utilized in the overall process. These are certain preferred embodiments, which are not intended to limit the present invention's scope. On the contrary, the present invention covers all alternatives, modifications, and equivalents as can be included within the scope of the claims, routine experimentation, including appropriate manipulation of the reaction conditions, reagents used, and sequence of the synthetic route, protection of any chemical functionality that can be compatible with the reaction conditions, and deprotection at suitable points in the reaction sequence of the method are included within the scope of the present invention.

EXAMPLE 1

(S)-Ethyl 2-(1-phenylethylamino)cyclohex-1-enecarboxylate (8)

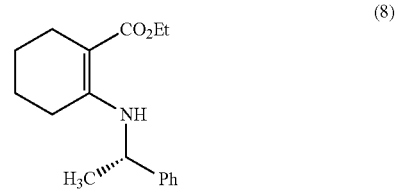

(8)

Ethyl 2-oxocyclohexane carboxylate (6, 484.9 g) and (S)-(−)-1-phenylethylamine (7, 362.5 g) were charged into an RB flask followed by heptanes (1.5 L) and Ytterbium (III) trifluoromethane sulfonate (8.8 g). The contents were heated to reflux for 3 hours and the liberated water was removed simultaneously and then cooled to 22° C. (±3° C.). The insoluble material was filtered and the filtrate was concentrate on a rotary evaporator under vacuum to afford 869.4 g of (S)-ethyl 2-(1-phenylethylamino)cyclohex-1-enecarboxylate (8) as an oil.

EXAMPLE 2

(1R,2S)-Ethyl 2-((S)-1-phenylethylamino)cyclohexanecarboxylate (9)

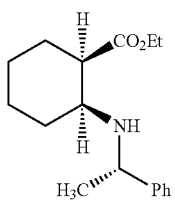

(9, Major isomer)

Acetic acid (1.0 L) was added to a reactor followed by sodium borohydride (100 g) with cooling between 16-30° C. under nitrogen in NLT 1 hour and mixed for NLT 30 minutes. Acetonitrile (500 mL) was added and mixed for NLT 30 minutes, and the cooled to below 5° C. A solution of (S)-ethyl 2-(1-phenylethylamino)cyclohex-1-enecarboxylate (8, 269 g) dissolved in acetonitrile (250 mL) was added in NLT 30 minutes, while maintaining the temperature between 2-8° C. and then the reaction mixture was warmed to 22° C., and mixed for NLT 4 hours. The mixture was cooled below 5° C. and quenched with 1.77 L of 25% aqueous sodium hydroxide solution, water (1.3 L) and heptanes (0.75 L) and the pH was adjusted pH to ~8.0. The organic layer was separated and the aqueous layer was extracted with heptanes (2×0.75 L), and then the combined heptane layers were washed with water (2×0.75 L) and 3.5 M aqueous sodium chloride solution (0.75 L). The heptane solution was then dried using anhydrous magnesium sulfate and concentrated under vacuum to afford 243.9 g of (1R,2S)-Ethyl 2-((S)-1-phenylethylamino)cyclohexanecarboxylate (9) as the major isomer.

EXAMPLE 3

(1S,2S)-Ethyl 2-((S)-1-phenylethyl amino)cyclohexanecarboxylate (10)

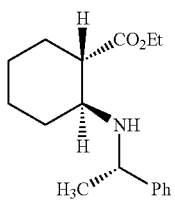

(10, Major isomer)

Tetrahydrofuran (1.25 L) was charged to a reactor followed by t-butanol (150 mL), and sodium t-butoxide (313 g) under nitrogen at ambient temperature. Additional tetrahydrofuran (1.0 L) was added and then the contents were cooled to <10° C. A solution of (1R,2S)-ethyl 2-((S)-1-phenylethylamino) cyclohexane carboxylate (9, 243.9 g) in tetrahydrofuran (300 mL) was added in NLT 30 minutes, while maintaining the temperature between 6-12° C. After the addition was complete, the mixture was warmed to 22° C. in NLT 30 minutes and further mixed for NLT 4 hours under nitrogen. The contents were cooled to <10° C. and the reaction was quenched with a solution of ammonium chloride (269.3 g) and water in NLT 30 minutes, while maintaining the temperature between 6-12° C. The lower aqueous layer was separated and extracted with 750 mL of heptanes. The upper organic layer was concentrated to about 0.8 L volume and extracted with the heptanes solution. The aqueous layer was separated and extracted with fresh heptanes (2×0.75 L) and the combined organic layers were washed with water (2×0.75 L) and 3.5 M aqueous sodium chloride solution (0.75 L), and dried with anhydrous magnesium sulfate. Concentration of the organic layer under vacuum gave 237.9 g of (1S,2S)-ethyl 2-((S)-1-phenylethyl amino)cyclohexane carboxylate (10) as a major isomer.

EXAMPLE 4

(1S,2S)-2-[(S)-1-Phenylethyl amino]cyclohexyl)methanol (11)

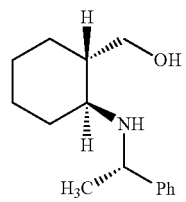

(11, Major isomer)

Tetrahydrofuran (1.9 L) was charged to a reactor and cooled to 15° C. and lithium borohydride (52.8 g) was added under nitrogen. A solution of (1S,2S)-Ethyl 2-((S)-1-phenylethylamino)cyclohexanecarboxylate (10, 237.9 g) in tetrahydrofuran (0.35 L) was added and the reaction mixture was heated to reflux for NLT 12 hours, under nitrogen. The mixture was cooled to below 10° C. and acetic acid (NLT 278 mL) was added, while maintaining the temperature between 5-15° C. in NLT 30 minutes. 25% aqueous sodium hydroxide solution (1.78 L) and water (~2 L) were added to adjust pH to ~8.7. The aqueous layer was separated and extracted with 2×0.75 L of heptanes, which was kept aside. The organic layer was concentrated to about 0.8 L volume and combined with the heptane extracts and additional water (0.75 L). The aqueous layer was separated and extracted with heptanes (0.75 L) and the combined organic extracts were washed with water (2×0.75 L), 3.5 M aqueous sodium chloride solution (0.75 L) and dried using anhydrous magnesium sulfate. The filtered solution was concentrated under vacuum and provided 184.1 g) of (1S,2S)-2-[(S)-1-phenylethyl amino]cyclohexyl)methanol (11) as the major isomer.

EXAMPLE 5

Ethyl 2-(((1S,2S)-2-(hydroxymethyl)cyclohexyl) ((S)-1-phenylethyl)amino)acetate (13)

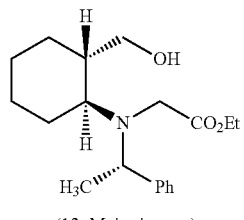

(13, Major isomer)

A solution of (1S,2S)-2-[(S)-1-phenylethyl amino]cyclohexyl)methanol (11) (339.1 g) dissolved in acetonitrile (2.2

L) was charged to a reactor followed by ethyl bromoacetate (12) (234.2 mL) and anhydrous sodium carbonate (224.2 g) under nitrogen. The contents were heated to reflux temperature for NLT 18 hours with vigorous agitation. Acetonitrile was distilled under vacuum to about 1 L volume, cooled to <30° C. and diluted with 0.75 L of heptanes and 1.0 L of water. The aqueous layer was separated and extracted with heptanes (2×0.75 L), and the combined organic layers were washed with water (0.75 L) followed by 0.75 L 3.5 M aqueous sodium chloride solution. The heptane layer was dried with anhydrous magnesium sulfate and concentrated under vacuum to afford 557.8 g of ethyl 2-((1S,2S)-2-(hydroxymethyl)cyclohexyl)((S)-1-phenylethyl)amino) acetate (13) as the major isomer.

EXAMPLE 6

Ethyl 2-(((1S,2S)-2-((methylsulfonyloxy)methyl)cyclohexyl)((S)-1-phenylethyl)amino) acetate (14)

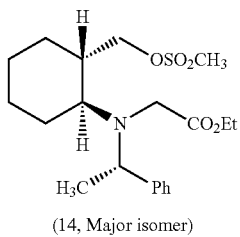

(14, Major isomer)

Dichloromethane (225 ml) was charged to a 1 L flask containing ethyl 2-(((1S,2S)-2-(hydroxymethyl)cyclohexyl)((S)-1-phenylethyl)amino)acetate (13) (22.4 g) and triethylamine (37.1 mL) was added and the entire solution was cooled to 5° C. under nitrogen. Methanesulfonyl chloride (15.5 mL) was added in NLT 10 minutes and the mixture was stirred for NLT 15 minutes at low temperature (between 2-10° C.). The reaction mixture was then warmed to 22° C. and stirred for NLT 1 hour and then quenched with 110 mL of ice-water while the stirring was continued for NLT 30 minutes. The lower organic layer was separated and the upper aqueous layer was extracted with 110 mL of dichloromethane. The combined organic layers were washed with water (2×110 mL), dried with anhydrous sodium sulfate and concentrated under vacuum to afford 30.1 g of ethyl 2-(((1S,2S)-2-((methylsulfonyloxy)methyl)cyclohexyl)((S)-1-phenylethyl)amino) acetate (14, major isomer) as a viscous oil.

EXAMPLE 7

(2S,3aR,7aS)-Ethyl 1-((S)-1-phenylethyl)octahydro-1H-indole-2-carboxylate (15)

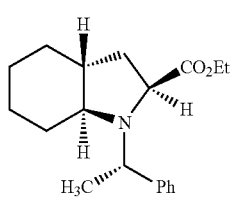

(15)

Tetrahydrofuran (210 mL) was charged to 1 L flask containing ethyl 2-(((1S,2S)-2-((methylsulfonyloxy)methyl)cyclohexyl)((S)-1-phenylethyl)amino)acetate (14, 30.1 g), sodium t-butoxide (9.6 g) was added at ambient temperature between 19-24° C. under nitrogen. The mixture was then heated to 65° C. and stirred for NLT 1 hour and cooled to 5° C. It was then quenched with a solution of ammonium chloride (10.69 g) in water (34 mL) and concentrated to about 100 mL volume. The mixture was diluted with heptanes (210 mL) and water (105 mL) and the aqueous layer is further extracted with heptanes (2×105 mL). The combined organic layers were washed with water (105 mL), followed by 3.5 M aqueous sodium chloride solution (105 mL). The heptane layer was dried with anhydrous sodium sulfate and concentrated under vacuum to afford 20.65 g of crude compound (15), which was purified on silica gel (700 g) chromatography using 3-4% ethyl acetate in hexanes to afford 8.24 g of (2S, 3aR,7aS)-ethyl 1-((S)-1-phenylethyl)octahydro-1H-indole-2-carboxylate (15) as a viscous oil.

EXAMPLE 8

(2S,3aR,7aS)-Ethyl octahydro-1H-indole-2-carboxylate (16)

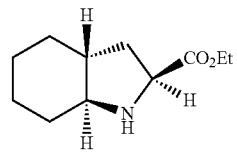

(16)

5% palladium on carbon (0.27 g) was added to a solution of (2S,3aR,7aS)-ethyl 1-((S)-1-phenylethyl)octahydro-1H-indole-2-carboxylate (15) (2.7 g) in ethanol (20 mL) and the mixture was heated at 60° C. under hydrogen (14.5 psi) atmosphere for NLT 3 hours. The catalyst was filtered and washed with fresh ethanol (15 mL). The combined filtrate was concentrated under vacuum to afford 1.93 g of (2S,3aR,7aS)-Ethyl octahydro-1H-indole-2-carboxylate (16) as a viscous oil.

EXAMPLE 9

(2S,3aR,7aS)-Octahydro-1H-indole-2-carboxylic acid hydrochloride (5)

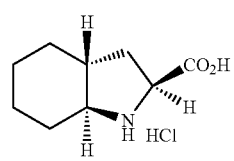

(5)

6 N hydrochloric acid (6 mL) was added to 0.42 g of (2S,3aR,7aS)-ethyl octahydro-1H-indole-2-carboxylate (16) and heated to reflux for NLT 4 hours. The mixture was concentrated and dried under vacuum to afford 0.42 g of (2S,3aR, 7aS)-octahydro-1H-indole-2-carboxylic acid hydrochloride (5) as a crystalline solid.

EXAMPLE 10

(S)-Ethyl 2-(1-phenylethylamino)cyclohex-1-enecarboxylate (8)

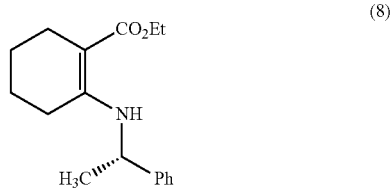

Ethyl 2-oxocyclohexane carboxylate (6, 170.2 g, 1.0 mol, 1.0 equiv.) and (S)-(–)-1-phenylethylamine (7, 126.0 g, 1.04 mol, 1.04 equiv., ee: >99%) were sequentially charged into a 1-L reaction flask fitted with a Dean-Stark trap, condenser and heating mantle with temperature controller probe containing toluene (500 mL). The solution was heated to reflux with agitation at 100-120° C. for NLT 3 h to azeotropically remove the theoretical amount of water (~18 mL, 1.0 mol). The reaction mixture was then cooled to 22±3° C. temperature. Resulting clear pale yellow solution containing the theoretical amount of (S)-ethyl 2-(1-phenylethylamino)cyclohex-1-enecarboxylate (8, 273.4 g, 1.0 mol) was used in the next step without purification or concentration. GC (Column: DB-5, Size: 0.53 mm×30 m): Temperature Gradient: 20 to 200° C. in 20 min and hold at 200° C. in 10 min, Injection temperature: 180° C., FID detector temperature: 280° C., $R_t$: 20.2 min, >99% (PA).

EXAMPLE 11

(1R,2S)-Ethyl 2)-((S)-1-phenylethylamino)cyclohexanecarboxylate hydrobromide (9)

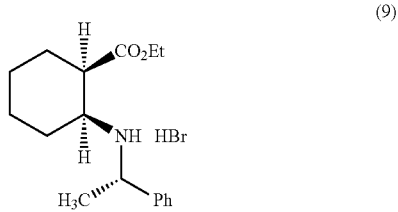

Isobutyric acid (1.86 L, 1.762 Kg, 20.0 mol, 20.0 equiv.) was added to a 4 L reactor under nitrogen and cooled to 2-5° C. temperature. Sodium borohydride (113.49 g, 3.0 mol, 3.0 mole equiv.) is added with agitation between 0-10° C. in NLT 2 h. The mixture warmed to 18° C. temperature and mixed for an additional NLT 15 min. The solution was cooled to –5° C. to –8° C. then the toluene solution containing the (S)-ethyl 2-(1-phenylethylamino)cyclohex-1-enecarboxylate (8, 273.37 g, 1.0 mol, 1.0 equiv.) was added over 50 min while maintaining the temperature at 0±2° C. The contents were mixed for 2 h and 40 min and quenched by the slow addition of 1 L of 4N hydrochloric acid while maintaining the temperature below 10° C. To this mixture, 2.1 L of 25 w/w % sodium hydroxide solution was added while maintaining the temperature at 5-20° C. The phases were allowed to settle and the upper layer organic was separated. The lower aqueous layer was extracted with of toluene (2×680 mL). The combined organic layers were washed sequentially with water (2×680 mL) and 3.5 M aqueous sodium chloride solution (2×680 mL). The toluene solution was then dried using anhydrous magnesium sulfate (30 g), filtered and concentrated under vacuum to afford 298.1 g of crude (1R,2S)-Ethyl 2-((S)-1-phenylethylamino)cyclohexanecarboxylate (9) free base, as an oil. The crude product was dissolved in 1.1 L of ethyl acetate in a 2 L reactor flask and cooled to –0.5° C. temperature. To this mixture, 247 mL of 30 wt. % hydrogen bromide in propionic acid was added with agitation over 1 h and 20 min, while maintaining the temperature at 0±2° C. The contents were stirred for an additional 1 h at 0° C. and the crystalline product was filtered and washed twice with 300 mL of cold (0° C.) ethyl acetate. The wet cake was dried at 45° C. temperature under vacuum for 5 h to afford 302.3 g of the desired (1R,2S)-Ethyl 2-((S)-1-phenylethylamino)cyclohexanecarboxylate hydrobromide salt (9). The dried hydrobromide salt (9,) and 2.47 L of acetonitrile was added to a 3 L reactor flask under nitrogen then heated to reflux at approximately 81-82° C. temperature. After the solids were dissolved, the clear solution was gradually cooled to 0° C. over 3 h period and held for 30 min at 0±2° C. temperature. The solids were filtered and washed with 200 mL of cold (0° C.) acetonitrile. The wet cake was dried at 40-45° C. temperature under vacuum for 18 h to afford 246.2 g of the purified (1R,2S)-Ethyl 2-((S)-1-phenylethylamino)cyclohexanecarboxylate hydrobromide salt in 69.1% yield, as a white powder. Analytical HPLC (Daicel Chiralpack AD-RH column, Size: 150×4.6 mm); 0.02 M Ammonium acetate buffer (pH: 7.7-7.8): Acetonitrile/50:50, 0.3 mL/min, Wave length: 220 nm, Column oven temperature: 55° C., $R_t$: 16.14 min, 99.75% (PA); $^1$H NMR (D$_2$O, 400 MHz): δ 7.56-7.50 (m, 5H), 4.62 (q, 1H, J=10.4, 6.8 Hz), 4.39-4.31 (m, 1H), 4.30-4.22 (m, 1H), 3.27-3.15 (m, 2H), 2.26-2.19 (m, 1H), 1.81-1.64 (m, 3H), 1.70 (d, 3H, J=6.8 Hz), 1.57-1.39 (m, 2H), 1.33 (t, 3 H, J=7.2 Hz), 1.30-1.18 (2H); LC-MS (m/z): 276.2 (M+H)$^+$.

EXAMPLE 12

(1S,2S)-Ethyl 2-((S)-1-phenylethyl amino)cyclohexanecarboxylate hydrochloride (10)

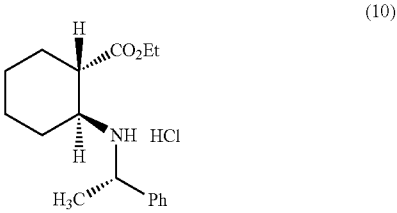

(1R,2S)-Ethyl 2-((S)-1-phenylethylamino)cyclohexanecarboxylate hydrobromide (9, 130 g, 0.356 mol, 1.0 equiv.) was added to a 2-L reactor containing 529 mL of 10% w/v sodium carbonate solution and 260 mL of heptanes at ambient temperature. The slurry was mixed rapidly at 18-25° C. for NLT 30 min. During this period, the solids were dissolved to form clear solution, which was allowed stand for NLT 10 min to for two clear layers. The phases were separated and retained both layers. The lower aqueous layer was extracted twice with 260 mL of heptanes. The heptanes extracts were combined and washed sequentially with 260 mL of tap water then 260 mL of 3.5 M sodium chloride solution. The heptanes extract was dried with anhydrous magnesium sulfate (10.4 g), filtered and concentrated under vacuum to afford 98.2 g of free base (9) as viscous oil. Anhydrous tetrahydrofuran (472 mL) was added to a 3-L clean/dry reactor, which was equipped with a mechanical stirrer, temperature probe under nitrogen. t-Butanol (70.2 mL) was added followed by sodium t-butoxide (70.2 g, 0.731 mol, 2.05 equiv.) carefully in portions under nitrogen atmosphere with cooling, while maintaining the temperature below 25° C. An additional 472 mL of anhydrous tetrahydrofuran was added as a rinse and then the contents were cooled to: 6-12° C. The (1R,2S)-ethyl 2-((S)-1-phenylethylamino)cyclohexane carboxylate (9) free base, which was prepared above was dissolved in 95 mL of anhydrous tetrahydrofuran and the solution was added via addition funnel to the sodium t-butoxide slurry while maintaining the temperature at 6-12° C. temperature under nitrogen over a period of approximately 45 min. After the addition was complete, the mixture was stirred for an additional 15 min at 6-12° C. temperature then the resulting pale yellow/off-white slurry was warmed to 19-25° C. and mixed for NLT 4 h under nitrogen. The contents were cooled to 6-12° C. and quenched using an 18 wt. % aqueous ammonium chloride solution (58.5 g ammonium chloride in 322 mL of water) while maintaining the temperature at 5-15° C. After mixing the contents for an additional 30 min at 20-25° C. temperature the layers were separated. The upper organic layer was separated and concentrated under vacuum at an internal temperature NMT 50° C. to an approximately ⅓ to ¼ final volume. The bottom aqueous lower layer in 3 L reaction flask was extracted with 3×259 mL of heptanes. The two heptanes extracts and the separately concentrated upper organic layer were combined and washed sequentially with 2×259 ml, of water and 2×259 ml, of 3.5 M aqueous sodium chloride solution. The heptanes solution was dried using anhydrous magnesium sulfate (10.4 g), filtered and concentrated on a rotary evaporator under vacuum at NMT 70° C. temperature. Residual solvents in the resulting crude product were removed using a high vacuum pump to afford 93 g of crude (1S,2S)-ethyl 2-((S)-1-phenylethylamino)cyclohexanecarboxylate (10) as pale yellow viscous oil. The crude (1S,2S)-ethyl 2-((S)-1-phenylethyl amino)cyclohexanecarboxylate (10) was dissolved in 332 mL of ethanol (2B, 200 proof) in a 1-L clean/dry reactor flask equipped with a mechanical stirrer, temperature probe under nitrogen with mixing. From a dropping funnel charge 117 mL of a solution of 14 wt. % hydrogen chloride in ethanol was added to the reactor over 5-10 min at NMT 40° C. temperature. The mixture was stirred for 30 min at less than 40° C. as a white solid precipitates. The mixture was heated to 65-75° C. to dissolve the solids and the contents were cooled slowly at approximately at rate of 10-15° C. per h to 0-5° C. temperature and held for 4 h. The white solid was collected via filtration and washed with 100 mL of cold (0° C.) ethanol (2B, 200 proof). The solid was dried in a vacuum oven at 45-50° C. temperature to afford 64.9 g of (1S,2S)-ethyl 2-((S)-1-phenylethylamino)cyclohexane carboxylate hydrochloride (10) in 58.5% as a white solid. Analytical HPLC (Daicel Chiralpack AD-RH column, Size: 150×4.6 mm); 0.02 M Ammonium acetate buffer (pH: 7.7-7.8): Acetonitrile/50:50, 0.3 mL/min, Wave length: 220 nm, Column oven temperature: 55° C., $R_t$: 16.00 min, 98.98% (PA); $^1$H NMR ($D_2O$, 400 MHz): δ 7.51-7.46 (m, 5H), 4.56 (q, 1H, J=13.9, 7.0 Hz), 4.27-4.14 (m, 2H), 3.47 (dt, 1H, J=11.4, 3.9 Hz), 2.58 (dt, 1H, J=11.6, 4.0 Hz), 2.17-2.10 (m, 1H), 1.91-1.84 (m, 1H), 1.75- 1.62 (m, 3H), 1.68 (d, 2H, J=6.8 Hz), 1.48-1.34 (m, 2H), 1.27 (t, 3H, J=7.2 Hz), 1.25-1.15 (m, 2H); LC-MS (m/z): 276.2 $(M+H)^+$.

EXAMPLE 13

(1S,2S)-Ethyl 2-((S)-1-phenylethyl amino)cyclohexanecarboxylate hydrochloride (10) Via the Recycling Method

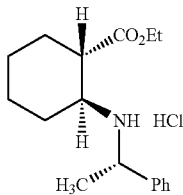

(10)

Mother liquor containing the hydrochloride salt of (1R,2S)-Ethyl 2-((S)-1-phenylethylamino)cyclohexane carboxylate (9) was concentrated and added to a 2-L reactor containing 493 mL of 10% w/v sodium carbonate solution and 216 mL of heptanes at ambient temperature. The slurry was mixed rapidly at 18-25° C. for NLT 30 min. During this period, the solids were dissolved to form clear solution, which was allowed stand for NLT 10 min to for two clear layers. The phases were separated and retained both layers. The lower aqueous layer was extracted twice with 216 mL of heptanes. The heptanes extracts were combined and washed sequentially with 216 mL of tap water then 216 mL of 3.5 M sodium chloride solution. The heptanes extract was dried with anhydrous magnesium sulfate (8.6 g), filtered and concentrated under vacuum to afford 56.8 g of free base (9, 0.206 mol, 1.0 equiv.) as viscous oil. Anhydrous tetrahydrofuran (260 mL) was added to a 2-L clean/dry reactor, which was equipped with a mechanical stirrer, temperature probe under nitrogen. t-Butanol (40.0 mL) was added followed by sodium t-butoxide (40.0 g, 0.416 mol, 2.02 equiv.) carefully in portions under nitrogen atmosphere with cooling, while maintaining the temperature below 25° C. An additional 269 mL of anhydrous tetrahydrofuran was added as a rinse and then the contents were cooled to: 6-12° C. The (1R,2S)-ethyl 2-((S)-1-phenylethylamino)cyclohexane carboxylate (9) free base, which was prepared above was dissolved in 54 mL of anhydrous tetrahydrofuran and the solution was added via addition funnel to the sodium t-butoxide slurry while maintaining the temperature at 6-12° C. temperature under nitrogen over a period of approximately 45 min. After the addition was complete, the mixture was stirred for an additional 15 min at 6-12° C. temperature then the resulting pale yellow/off-white slurry was warmed to 19-25° C. and mixed for NLT 4 h under nitrogen. The contents were cooled to 6-12° C. and quenched using an 18 wt. % aqueous ammonium chloride solution (33.3 g ammonium chloride in 184 mL of water) while maintaining the temperature at 5-15° C. After mixing the contents for an additional 30 min at 20-25° C. temperature the layers were separated. The upper organic layer was separated and concentrated under vacuum at an internal temperature NMT 50° C. to an approximately ⅓ to ¼ final volume. The bottom aqueous lower layer in 3 L reaction flask was extracted with 3×148 mL of heptanes. The two heptanes extracts and the separately concentrated upper organic layer were combined and washed sequentially with 2×148 mL of water and 2×148 mL of 3.5 M aqueous sodium chloride solution. The heptanes solution was dried using anhydrous magnesium sulfate (5.9 g), filtered and concentrated on a rotary evaporator under vacuum at NMT 70° C. temperature. Residual solvents in the resulting crude product were removed using a high vacuum pump to afford 53.7 g of crude (1S,2S)-ethyl 2-((S)-1-phenylethylamino)cyclohexanecarboxylate (10) as pale yellow viscous oil. The crude (1S,2S)-ethyl 2-((S)-1-phenylethylamino)cyclohexanecarboxylate (10) was dissolved in 192 mL of ethanol (2B, 200 proof) in a 1-L clean/dry reactor flask equipped with a mechanical stirrer, temperature probe under nitrogen with mixing. From a dropping funnel charge 68 mL of a solution of 14 wt. % hydrogen chloride in ethanol was added to the reactor over 5-10 min at NMT 40° C. temperature. The mixture was stirred for 30 min at less than 40° C. as a white solid precipitates. The mixture was heated to 65-75° C. to dissolve the solids and the contents were cooled slowly at approximately at rate of 10-15° C. per h to 0-5° C. temperature and held for 4 h. The white solid was collected via filtration and washed with 58 mL of cold (0° C.) ethanol (2B, 200 proof). The solid was dried in a vacuum oven at 45-50° C. temperature to afford 32 g of (1S,2S)-ethyl 2-((S)-1-phenylethylamino)cyclohexane carboxylate hydrochloride (10) in 49.8% as a white solid. Analytical HPLC (Daicel Chiralpack AD-RH column, Size: 150×4.6 mm); 0.02 M Ammonium acetate buffer (pH: 7.7-7.8): Acetonitrile/50:50, 0.3 mL/min, Wave length: 220 nm, Column oven temperature: 55° C., $R_t$: 16.01 min, 98.63% (PA).

EXAMPLE 14

(1S,2S)-2-[(S)-1-Phenylethyl amino]cyclohexyl) methanol (11)

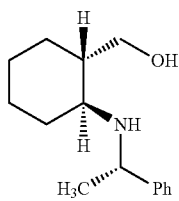

(11)

Charge (1S,2S)-ethyl 2-((S)-1-phenylethylamino)cyclohexane carboxylate hydrochloride (10, 163.5 g, 0.524 mol, 1.0 equiv.) to a 2-L reactor containing 788 mL of 10% w/v sodium carbonate solution and 327 mL of heptanes at ambient temperature. Mix the contents rapidly at 18-25° C. for NLT 30 min. During this period, the solids were dissolved and agitation was stopped for NLT 10 min to form two clear layers. Separate the phases and retain both layers. Extract the lower aqueous layer twice with 327 mL of heptanes each. Combine all heptanes extracts and wash sequentially with 327 mL of tap water then 327 mL of 3.5 M aqueous sodium chloride solution. Dry the heptanes solution with anhydrous magnesium sulfate (13.5 g), filter and concentrate under vacuum to yield 148.9 g of (1S,2S)-ethyl 2-((S)-1-phenylethyl amino)cyclohexane carboxylate (>99% yield and contains residual heptanes) free base as an oil. Charge 1154 mL of tetrahydrofuran to the free base in a clean/dry 4 L reactor flask under nitrogen at ambient temperature, which is equipped with mechanical stirrer, thermocouple, and begin agitation. At ambient temperature, charge potassium borohydride (42.4 g, 0.786 mol, 1.5 mol equiv.) followed by lithium chloride (33.3 g, 0.785 mol, 1.5 mol equiv.) under nitrogen. The reaction mixture was heated to reflux (67° C.) with agitation and continue for NLT 12 h under nitrogen atmosphere. The mixture was cooled to below 22° C. temperature and charged 1734 mL of tap water over 20 min period using an addition funnel, while maintaining the temperature at NMT 27° C. The contents were mixed for an additional 30 min at ambient temperature and allowed the layers to separate. The upper organic layer was separated and concentrated using a rotary evaporator at NMT 50° C. temperature to yield crude product (11), as viscous oil. The lower aqueous layer was extracted three times with 327 mL of heptanes each. Combined the heptanes extracts were mixed with the concentrated viscous oil and wash the combined heptanes solution was sequentially washed with 327 mL of water and 327 mL of 3.5 M aqueous sodium chloride solution. The heptanes solution was dried with anhydrous magnesium sulfate (13.5 g), filtered and concentrated using vacuum at a temperature NMT 70° C. The resulting crude product was further dried using a high vacuum pump (~0.2 mmHg) for NLT 12 h period to afforded 120.9 g of (1S,2S)-2-[(S)-1-Phenylethylamino]cyclohexyl) methanol (11) as a viscous oil, which was carried to the next step without further purification. Analytical HPLC (Daicel Chiralpack AD-RH column, Size: 150×4.6 mm); 0.02 M Ammonium acetate buffer (pH: 7.7-7.8): Acetonitrile/50:50, 0.3 mL/min, Wave length; 220 nm, Column oven temperature: 55° C., $R_t$: 18.39 min, 98.66% (PA); LC-MS (m/z): 234.2 $(M+H)^+$.

EXAMPLE 15

Ethyl 2-(((1S,2S)-2-(hydroxymethyl)cyclohexyl) ((S)-1-phenylethyl)amino)acetate (13)

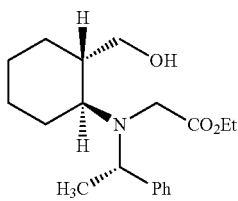

(13)

A solution of (1S,2S)-2-[(S)-1-phenylethylamino]cyclohexyl)methanol (11, 120.9 g, 0.524 mol, 1.0 equiv. based on HCl salt 10) dissolved in acetonitrile (610 mL) was charged to a 2 L reactor, which is equipped with mechanical stirrer and thermocouple under nitrogen atmosphere. To this solution, ethyl bromoacetate (12, 104.9 g, 0.628 mol, 1.2 equiv.) and anhydrous sodium bicarbonate (57.2 g, 0.681 mol, 1.3 equiv.) were added sequentially with agitation. The contents were heated to reflux temperature for NLT 18 h with vigorous agitation under nitrogen atmosphere. Acetonitrile was distilled out under vacuum to about 300 mL volume and the mixture was cooled to less than 30° C. temperature and diluted with 327 ml, of heptanes and 423 mL of water. The contents were mixed for NLT 15 min and allowed settle to form two layers. The bottom aqueous layer was separated and further extracted with 2×327 mL of heptanes. The two heptanes extracts were combined with the organic layer in the reactor and washed sequentially with 1×327 mL of water and 1×327 mL 3.5 M aqueous sodium chloride solution. The heptanes solution was dried using anhydrous sodium sulfate (13.5 g), filtered and concentrated under vacuum at NMT 60° C. temperature. The crude product was further dried under vacuum to afford 171.4 g of ethyl 2-(((1S,2S)-2-(hydroxymethyl)cyclohexyl)((S)-1-phenylethyl)amino) acetate (13) as viscous oil, which was carried to the next step without further purification. Analytical HPLC (Daicel Chiralpack AD-RH column, Size: 150×4.6 mm); 0.02 M Ammonium acetate buffer (pH: 7.7-7.8): Acetonitrile/50:50, 0.3 mL/min, Wave length: 220 nm, Column oven temperature: 55° C., $R_t$: 23.62 min; LC-MS (m/z): 320.2 (M+H)$^+$.

EXAMPLE 16

Ethyl 2-(((1S,2S)-2-((methylsulfonyloxy)methyl) cyclohexyl)((S)-1-phenylethyl)amino)acetate (14)

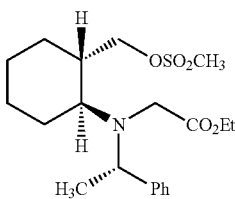

(14)

A solution of 167.4 g of ethyl 2-(((1S,2S)-2-(hydroxymethyl)cyclohexyl)((S)-1-phenylethyl)amino)acetate (13, 0.524 mol, 1.0 equiv. based on HCl salt 10) dissolved in 685 mL of dichloromethane was added to a 2 L reactor, which is equipped with mechanical stirrer and thermocouple under nitrogen atmosphere. To this solution, 63.8 g of triethylamine (0.629 mol, 1.2 equiv.) was added and the mixture was cooled to less than 5° C. temperature. 66 g (0.576 mol, 1.1 equiv.) of methanesulfonyl chloride was added dropwise while maintaining the temperature below 10° C. and after the addition was complete, the mixture was stirred for an additional 30 min and then warmed to approximately 20° C. temperature under nitrogen atmosphere. The reaction mixture was stirred for NLT 1 h and quenched with 261 mL of ice-water at below 25° C. temperature and mixed for NLT 15 min. The lower organic layer was separated and the upper aqueous layer was extracted with 2×135 mL of dichloromethane. The combined organic layers were washed with 3×327 mL of water, dried using anhydrous magnesium sulfate (13.5 g), filtered and concentrated on a rotary evaporator under vacuum at NMT 60° C. temperature. The resulting crude product (viscous oil) was dried over night using a high vacuum pump to afford 204.7 g of ethyl 2-(((1S,2S)-2-((methylsulfonyloxy)methyl) cyclohexyl) ((S)-1-phenylethyl)amino) acetate (14) as a viscous oil, which was carried to the next step without further purification. Analytical HPLC (Daicel Chiralpack AD-RH column, Size: 150×4.6 mm); 0.02 M Ammonium acetate buffer (pH: 7.7-7.8): Acetonitrile/50:50, 0.3 mL/min, Wave length: 220 nm, Column oven temperature: 55° C., $R_t$: 17.23 min; LC-MS (m/z): 398.2 (M+H)$^+$.

EXAMPLE 17

(2S,3aR,7aS)-Ethyl 1-((S)-1-phenylethyl)octahydro-1H-indole-2-carboxylate (15)

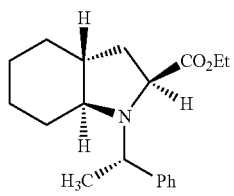

(15)

1.18 L of Anhydrous tetrahydrofuran was added to 2 L reactor, reactor, which is equipped with mechanical stirrer and thermocouple under nitrogen atmosphere. With mixing, 60.4 g of sodium t-butoxide (0.628 mol, 1.2 equiv.) was added and the mixture was cooled to below 10° C. temperature. During this period, the solids were dissolved to form an slightly hazy solution. To this mixture, a solution of 204.7 g of ethyl 2-(((1S,2S)-2-((methylsulfonyloxy)methyl)cyclohexyl)((S)-1-phenylethyl)amino)acetate (14, 0.524 mol, 1.0 equiv. based on HCl salt 10) in 297 mL of anhydrous tetrahydrofuran was added over a period of NLT 30 min, while maintaining the temperature below 10° C. The reaction mixture was warmed to 20±3° C. and mixed for NLT 3 h under nitrogen atmosphere. The reaction was then quenched using a solution of 50.3 g of ammonium chloride (0.942, 1.8 equiv.) in 267 mL of water, slowly. The phases were allowed to separate and the upper tetrahydrofuran layer was separated and concentrated on a rotary evaporator at NMT 50 temperature to an orange colored product residue. The lower aqueous layer was extracted with 2×495 mL of heptanes. The heptanes extracts were combined with the concentrated product residue and washed with 2×495 mL of 3.5 M aqueous sodium chloride solution. The heptanes extract was dried using anhydrous magnesium sulfate (13.5 g), filtered and concentrated on a rotary evaporator at NMT 70° C. temperature under vacuum. The resulting oil was further dried overnight under high vacuum to afford 124.3 g of crude (2S,3aR,7aS)-ethyl 1-((S)-1-phenylethyl)octahydro-1H-indole-2-carboxylate (15) as a major isomer (de: >97%), which was carried to the next step without further purification. Analytical HPLC (Daicel Chiralpack AD-RH column, Size: 150×4.6 mm); 0.02 M Ammonium acetate buffer (pH: 7.7-7.8): Acetonitrile/50:50, 0.3 mL/min, Wave length: 220 nm, Column oven temperature: 55° C., $R_t$: 28.59 min; LC-MS (m/z): 302.2 (M+H)$^+$.

On a smaller batch size, the reaction crude product 15 was isolated by starting from 30.14 g of crude ethyl 2-(((1S,2S)-2-((methyl sulfonyloxy)methyl)cyclohexyl)((S)-1-phenylethyl)amino)acetate [14, which was prepared from 15.0 g of ethyl 2-oxocyclohexane carboxylate (6, 0.0882 mol)] was purified silica gel column chromatography using 2-5% Ethyl acetate in hexanes. The combined product fraction pool was concentrated on a rotary evaporator at NMT 60° C. to afford 8.24 g of (2S,3aR,7aS)-ethyl 1-((S)-1-phenylethyl)octahydro-1H-indole-2-carboxylate (15) was isolated as a major isomer (de: >97%). Analytical HPLC (Daicel Chiralpack AD-RH column, Size: 150×4.6 mm); 0.02 M Ammonium acetate buffer (pH: 7.7-7.8): Acetonitrile/50:50, 0.3 mL/min, Wave length: 220 nm, Column oven temperature: 55° C., $R_t$: 28.33 min, 98.13% (PA); $^1$H NMR (CDCl$_3$, 400 Mz): δ 7.38-7.34 (m, 2H), 7.27-7.22 (m, 2H), 7.19-7.14 (m, 1H), 4.01 (q, 1H, J=13.6, 6.8 Hz), 3.91-3.84 (m, 1H), 5.83-3.76 (m, 1H), 3.50 (dd, 1H, J=10.6, 2.0 Hz), 2.20-2.10 (m, 1H), 1.84-1.77 (m, 2H), 1.75-1.52 (m, 5H), 1.34 (d, 3H, J=6.8 Hz), 1.24-0.96 (m, 4H), 1.08 (t, 3H, J=7.1 Hz); $^{13}$C NMR (CDCl$_3$): δ 175.4, 143.9, 127.8, 127.5, 126.3, 67.9, 60.2, 59.4, 57.9, 43.7, 35.6, 32.0, 30.4, 26.0, 25.0, 15.6, 14.4; LC-MS (m/z): 302.2 (M+H)$^+$.

EXAMPLE 18

(2S,3aR,7aS)-Ethyl octahydro-1H-indole-2-carboxylate Hydrochloride (16)

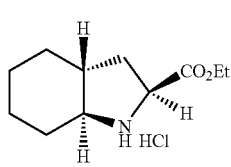

127 g of Raney Nickel (WR Grace 2800, water slurry) was added to a solution of 127.2 g of (2S,3aR,7aS)-ethyl 1-((S)-1-phenylethyl)octahydro-1H-indole-2-carboxylate (15) in 400 mL ethanol and the solution was mixed at room temperature in a Parr shaker apparatus for 30 min under Argon. The catalyst was filtered off and washed with 400 mL of ethanol. To this pre-treated product solution was added 21.7 g of palladium hydroxide on carbon (Degussa, 50 wt. % water). The mixture was hydrogenated for 1.5 h at 50° C. under 30 psig of hydrogen pressure. The catalyst was filtered and washed with fresh ethanol (100 mL). The hydrogenated product mixture was concentrated under vacuum at NMT 70° C. The resulting oil was added from a dropping funnel over 10-20 min at a temperature range of 25-35° C. to a 500 mL flask containing 263 g of a 14% ethanolic hydrogen chloride solution. The mixture was stirred for 1 h at ambient temperature then concentrated on a rotary evaporator to remove solvent under vacuum at 50-60° C. 400 mL of ethyl acetate was added to the residue and the mixture warmed to 35° C. The mixture was cooled to 22° C. over 30 min to form a precipitate. The slurry was cooled to 0-5° C. and held for 2 h. The solids were collected and washed with 20 mL of 0-5° C. ethyl acetate. The solids were vacuum dried in an oven at 45° C. to afford 34.0 g of (2S,3aR,7aS)-Ethyl octahydro-1H-indole-2-carboxylate hydrochloride salt (16). Analytical HPLC (Daicel Chiralpack AD-RH column, Size: 150×4.6 mm); 0.02 M Ammonium acetate buffer (pH: 7.7-7.8): Acetonitrile/50:50, 0.3 mL/min, Wave length: 220 nm, Column oven temperature: 55° C., $R_t$: 16.21 min, 97.95% (PA); $^1$H NMR (D$_2$O, 400 MHz): δ 4.52 (dd, 1H, J=11.2, 2.9 Hz), 4.30 (q, 2H, J=14.2, 7.16 Hz), 2.94 (dt, 1H, J=11.8, 3.6 Hz), 2.42-2.34 (m, 1H), 2.22-2.15 (m, 1H), 2.12-1.98 (m, 2H), 1.95-1.87 (m, 1H), 1.80-1.73 (m, 1H), 1.72-1.52 (m, 2H), 1.35-1.11 (m, 2H), 1.30 (t, 3H, J=7.1 Hz); LC-MS (m/z): 198.2 (M+H)$^+$.

EXAMPLE 19

(2S,3aR,7aS)-Octahydro-1H-indole-2-carboxylic acid hydrochloride (5)

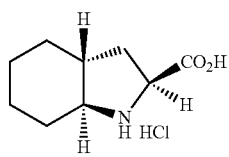

In a 500 mL reaction flask equipped with a distillation head was added 33.5 g (0.143 mol, 1.0 equiv.) of (2S,3aR,7aS)-Ethyl octahydro-1H-indole-2-carboxylate hydrochloride (16), 102 g of water, and 102 g of conc. hydrochloric acid. The contents were heated to 94-96° C. temperature with mixing for NLT 6 h while collecting about 9 mL of distillate at atmospheric pressure. The reaction mixture was cooled to room temperature and concentrated to dryness on a rotary evaporator. To the resulting crude product, 255 mL of acetonitrile was added and heated for 1 h at reflux with mixing to break up and dissolve the solids. The mixture was cooled gradually to 0-5° C. temperature at a rate of 10-15° C. per h, and held at 0-5° C. for NLT 2 h under nitrogen atmosphere. The solids were collected via filtration and washed with 10-20 mL of chilled (0-5° C.) acetonitrile. The product was dried at 45° C. under vacuum for 16 h to afford 25.6 g of (2S,3aR,7aS)-Octahydro-1H-indole-2-carboxylic acid hydrochloride (5) in 86.9% yield as a white solid. $^1$H NMR (D$_2$O, 400 MHz): δ 4.42 (dd, 1H, J=11.1, 2.7 Hz), 2.93, (dt, 1H, J=11.8, 3.6 Hz), 2.36 (ddd, 1H, J=12.9, 6.7, 2.7 Hz), 2.31-2.16 (m, 1H), 2.11-2.01 (m, 2H), 1.92-1.90 (m, 1H), 1.79-1.75 (m, 1H), 1.68-1.53 (m, 2H), 1.34-1.13 (m, 3H); LC-MS (m/z): 170.1 (M+H)$^+$. The isolated product (5) correlates to the material prepared according to U.S. Pat. No. 487,932 and *Tetrahedron Lett.*, 1992, 33, 4889.

Further, (2S,3aR,7aS)-Octahydro-1H-indole-2-carboxylic acid hydrochloride (5, 25.0 g, 0.122 mol) is converted to the corresponding benzyl ester [(2S,3aR,7aS)-Benzyl octahydro-1H-indole-2-carboxylate hydrochloride] using thionyl chloride, benzyl alcohol in dichloromethane in 90.1% yield (32.7 g) and the product was correlated by HPLC and NMR to the to the material prepared according to U.S. Pat. No. 487,932 and *Tetrahedron Lett.* 1992, 33, 4889. Analytical HPLC (Daicel Chiralpack AD-RH column, Size: 150×4.6 mm); 0.02 M Ammonium acetate buffer (pH: 7.7-7.8): Acetonitrile/50:50, 0.3 mL/min, 220 nm, Column chamber temperature: 55° C., $R_t$: 32.6 min, 99.34% (PA); $^1$H NMR (D$_2$O, 400 MHz): δ 7.49-7.43 (m, 5H), 5.37-5.28 (q, 2H, J=23.2, 12.0 Hz), 4.60 (dd, 1H, J=11.2, 2.9 Hz), 2.95, (dt, 1H, J=11.8, 3.7 Hz), 2.36 (ddd, 1H, J=13.1, 6.9, 2.9 Hz), 2.25-2.15 (m, 1H), 2.13-2.02 (m, 2H), 2.03-1.96 (m, 1H), 1.95-1.88 (m, 1H), 1.65-1.53 (m, 2H), 1.32-1.12 (m, 3H); LC-MS (m/z): 274.1 (M+H)$^+$.

EXAMPLE 20

((1S,2S)-2-Aminocyclohexyl)methanol (17)

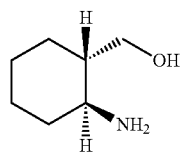

5% Palladium on carbon (0.05 g) was added to a solution of (1S,2S)-2-[(S)-1-phenylethyl amino]cyclohexyl)methanol (11, 0.5 g, 0.002 mol) dissolved in methanol (15 mL). The mixture was heated at 60° C. under hydrogen (14.5 psi) atmosphere for NLT 3 h. The mixture was cooled to room temperature, flushed with nitrogen, the catalyst was filtered and washed with fresh methanol (10 mL). The combined filtrate was concentrated under vacuum to afford 0.28 g of ((1S,2S)-2-aminocyclohexyl)methanol (17) in quantitative yield as a white solid. $[\alpha]^{23}_D$ 9.1 (c, 0.0107 CHCl$_3$), $^1$H NMR (CDCl$_3$, 400 MHz): δ 3.61-3.54 (m, 2 H), 2.71 (bs, 3H), 2.45 (dt, 1H, J=10.6, 1.2 Hz), 1.85-1.78 (m, 1H), 1.74-1.65 (m, 1H), 1.62-1.53 (m, 1H), 1.40-1.30 (m, 1H), 1.25-1.06 (m, 3H), 0.91-0.80 (m, 1H), $^{13}$C NMR (CDCl$_3$): δ 70.2, 57.4, 45.5, 40.1, 28.6, 25.5, 25.5, For NMR of its enantiomer, ((1R,2R)-2-Aminocyclohexyl)methanol, see reference *J. Am. Chem. Soc.* 1996, 118, 5502.

The invention claimed is:

1. A process for preparing (2S,3aR,7aS)-Octahydro-1H-indole-2-carboxylic acid hydrochloride (5) comprising the steps of:

(a) N-alkylation of (1S,2S)-2-[(S)-1-phenylethyl amino] cyclohexyl)methanol (11) with ethyl chloroacetate or ethyl bromoacetate in the presence of a base to give ethyl 2-(((1S,2S)-2-(hydroxymethyl)cyclohexyl)((S)-1-phenylethyl)amino)acetate (13),

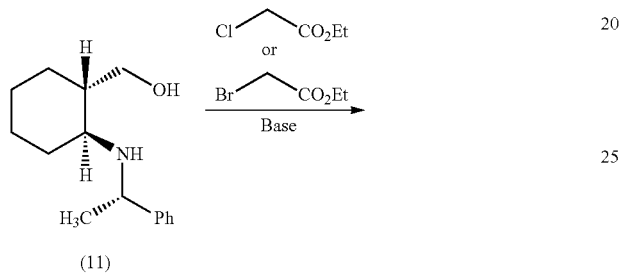

(b) conversion of ethyl 2-(((1S,2S)-2-(hydroxymethyl)cyclohexyl)((S)-1-phenylethyl)amino)acetate (13) to a compound of formula (14) wherein R$_3$ is a leaving group selected from the group consisting of mesylate, triflate, tosylate, methanesulfonate ester, trifluoromethane sulfonate ester, chloride, bromide, and iodide,

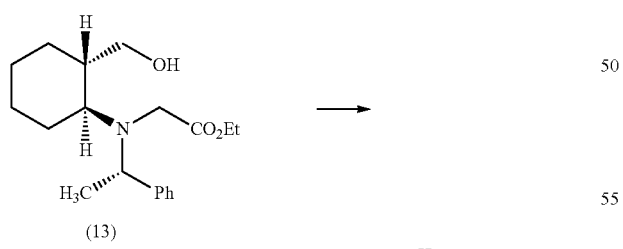

(c) treatment of the compound of formula (14) with a base to provide (2S,3aR,7aS)-ethyl 1-((S)-1-phenylethyl)octahydro-1H-indole-2-carboxylate (15),

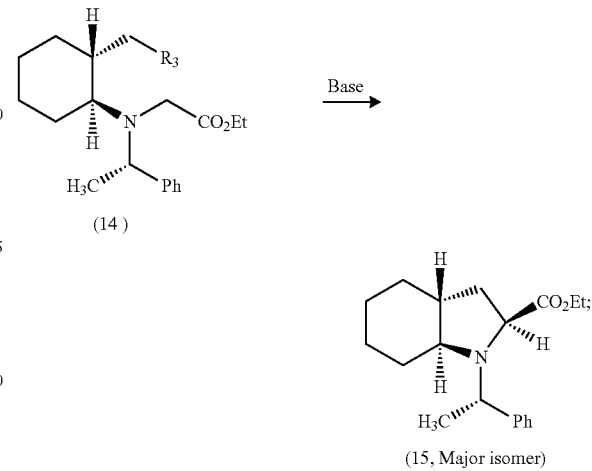

(d) cleavage of the N-α-methylbenzyl group of (2S,3aR,7aS)-ethyl 1-((S)-1-phenylethyl)octahydro-1H-indole-2-carboxylate (15) by hydrogenolysis to afford (2S,3aR,7aS)-ethyl octahydro-1H-indole-2-carboxylate (16), optionally followed by acidification to provide the hydrochloride salt of the compound of formula (16),

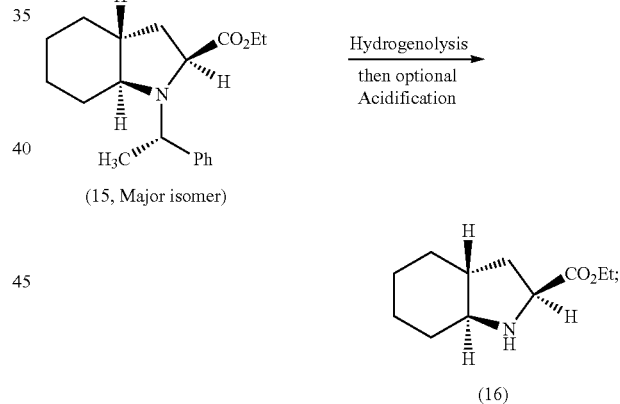

and (e) acid hydrolysis of (2S,3aR,7aS)-ethyl octahydro-1H-indole-2-carboxylate (16) or the hydrochloride salt thereof to provide (2S,3aR,7aS)-octahydro-1H-indole-2-carboxylic acid hydrochloride (5),

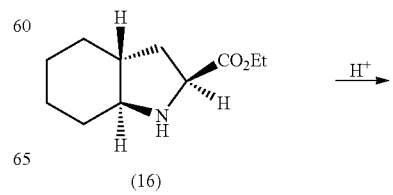

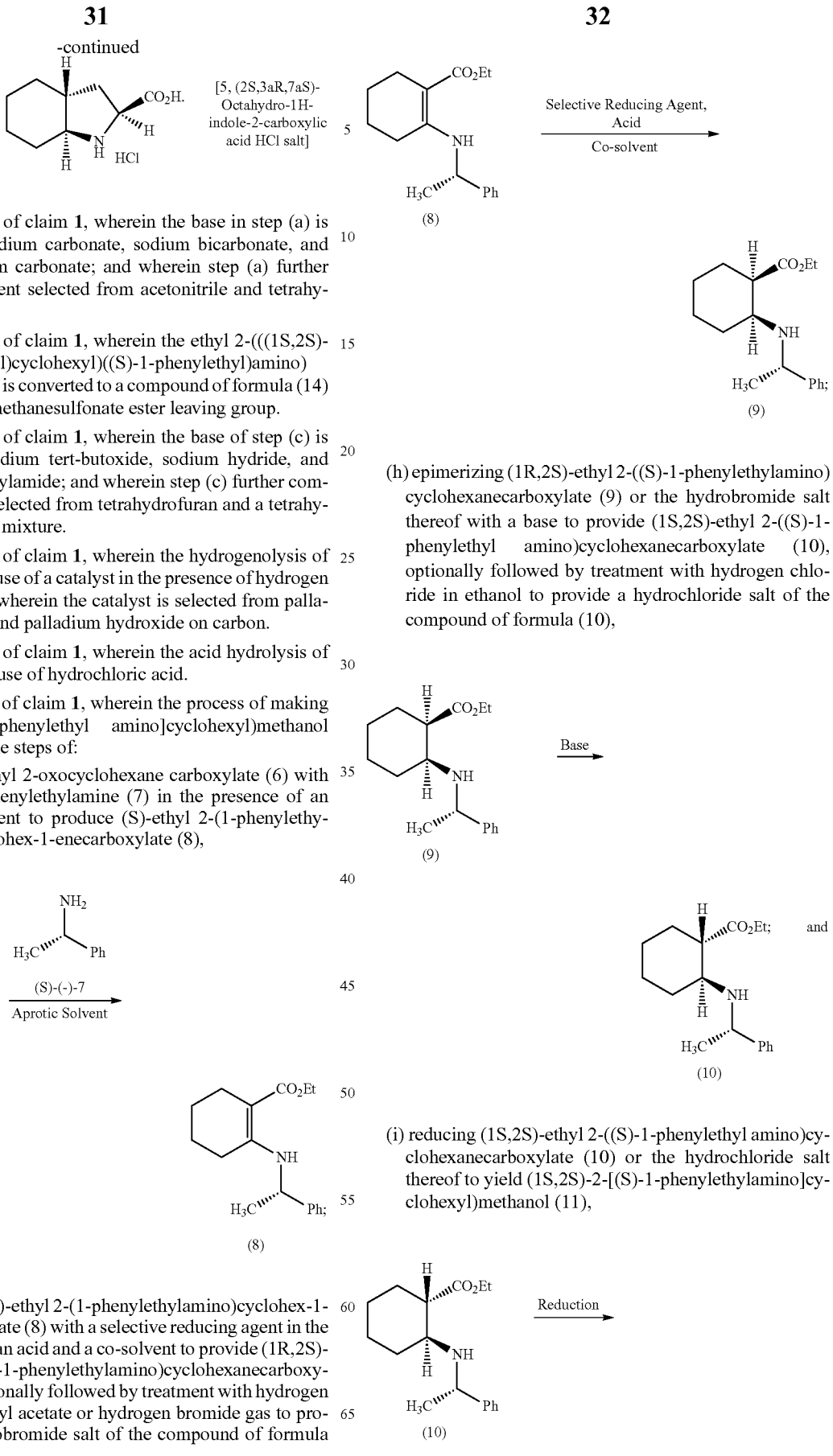

2. The process of claim 1, wherein the base in step (a) is selected from sodium carbonate, sodium bicarbonate, and potassium sodium carbonate; and wherein step (a) further comprises a solvent selected from acetonitrile and tetrahydrofuran.

3. The process of claim 1, wherein the ethyl 2-(((1S,2S)-2-(hydroxymethyl)cyclohexyl)((S)-1-phenylethyl)amino) acetate of step (b) is converted to a compound of formula (14) wherein $R_3$ is a methanesulfonate ester leaving group.

4. The process of claim 1, wherein the base of step (c) is selected from sodium tert-butoxide, sodium hydride, and lithium diisopropylamide; and wherein step (c) further comprises a solvent selected from tetrahydrofuran and a tetrahydrofuran/heptane mixture.

5. The process of claim 1, wherein the hydrogenolysis of step (d) includes use of a catalyst in the presence of hydrogen gas and ethanol, wherein the catalyst is selected from palladium on carbon and palladium hydroxide on carbon.

6. The process of claim 1, wherein the acid hydrolysis of step (e) includes use of hydrochloric acid.

7. The process of claim 1, wherein the process of making (1S,2S)-2-[(S)-1-phenylethyl amino]cyclohexyl)methanol (11) comprises the steps of:

(f) reacting ethyl 2-oxocyclohexane carboxylate (6) with (S)-(−)-1 phenylethylamine (7) in the presence of an aprotic solvent to produce (S)-ethyl 2-(1-phenylethylamino)cyclohex-1-enecarboxylate (8), (g) reducing (S)-ethyl 2-(1-phenylethylamino)cyclohex-1-enecarboxylate (8) with a selective reducing agent in the presence of an acid and a co-solvent to provide (1R,2S)-ethyl 2-((S)-1-phenylethylamino)cyclohexanecarboxylate (9), optionally followed by treatment with hydrogen bromide-ethyl acetate or hydrogen bromide gas to provide a hydrobromide salt of the compound of formula (9), (h) epimerizing (1R,2S)-ethyl 2-((S)-1-phenylethylamino) cyclohexanecarboxylate (9) or the hydrobromide salt thereof with a base to provide (1S,2S)-ethyl 2-((S)-1-phenylethyl amino)cyclohexanecarboxylate (10), optionally followed by treatment with hydrogen chloride in ethanol to provide a hydrochloride salt of the compound of formula (10), (i) reducing (1S,2S)-ethyl 2-((S)-1-phenylethyl amino)cyclohexanecarboxylate (10) or the hydrochloride salt thereof to yield (1S,2S)-2-[(S)-1-phenylethylamino]cyclohexyl)methanol (11), -continued

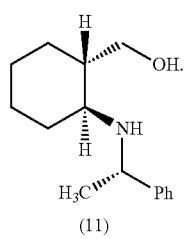

(11)

8. The process of claim 7, wherein the aprotic solvent of step (f) is selected from toluene and acetonitrile.

9. The process of claim 7, wherein the selective reducing agent of step (g) is selected from sodium borohydride and N-Selectride; wherein the acid is selected from acetic acid, isobutyric acid, pivalic acid, benzoic acid, trifluoroacetic acid, and phenylacetic acid; and wherein the co-solvent is selected from toluene and acetonitrile.

10. The process of claim 7, wherein the base of step (h) is selected from sodium tert-butoxide and lithium hexamethyldisilazide; and wherein step (h) further comprises a solvent selected from tetrahydrofuran, tert-butanol, and a tetrahydrofuran/tert-butanol mixture.

11. The process of claim 7, wherein the (1S,2S)-ethyl 2-((S)-1-phenylethyl amino)cyclohexanecarboxylate (10) or the hydrochloride salt thereof of step (i) is reduced with a reducing agent selected from lithium borohydride, and potassium borohydride in the presence of lithium chloride; and wherein step (i) further comprises a tetrahydrofuran co-solvent.

12. The process of claim 7, wherein the reduction of (S)-ethyl 2-(1-phenylethylamino)cyclohex-1-enecarboxylate (8) in step (g) is alternatively achieved using catalytic hydrogenation comprising a catalyst selected from carbon supported nanoparticles (Pt/C), and a hydrogenating agent selected from acetic acid.

13. The process of claim 1, wherein the process of making (1S,2S)-2-[(S)-1-phenylethyl amino]cyclohexyl)methanol (11) comprises the steps of:

(f) reacting ethyl 2-oxocyclohexane carboxylate (6) with (S)-(−)-1 phenylethylamine (7) in the presence of a Lewis acid catalyst in aprotic solvent to produce (S)-ethyl 2-(1-phenylethylamino)cyclohex-1-enecarboxylate (8),

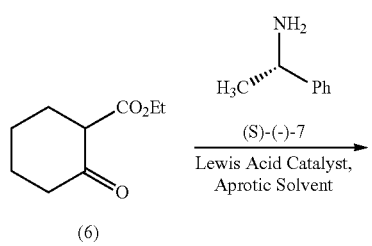

(6)

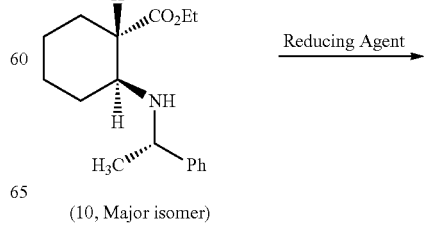

(8)

(g) reducing the (S)-ethyl 2-(1-phenylethylamino)cyclohex-1-enecarboxylate (8) with a selective reducing agent in the presence of a co-solvent to produce (1R,2S)-ethyl 2-((S)-1-phenylethylamino)cyclohexanecarboxylate (9),

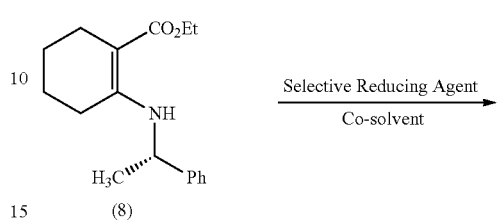

(8)

(9)

(h) epimerizing (1R,2S)-ethyl 2-((S)-1-phenylethylamino) cyclohexanecarboxylate (9) with a base to provide (1S, 2S)-ethyl 2-((S)-1-phenylethyl amino)cyclohexanecarboxylate (10),

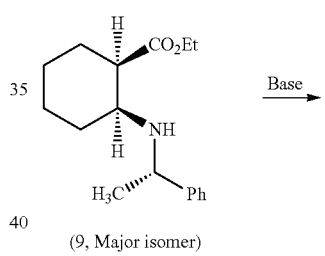

(9, Major isomer)

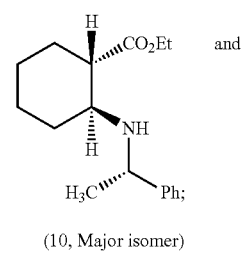

(10, Major isomer)

(i) reducing the (1S,2S)-ethyl 2-((S)-1-phenylethyl amino) cyclohexanecarboxylate (10) to yield (1S,2S)-2-[(S)-1-phenylethylamino]cyclohexyl)methanol (11),

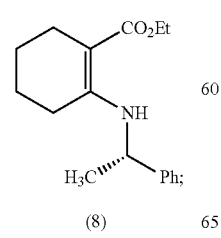

(10, Major isomer)

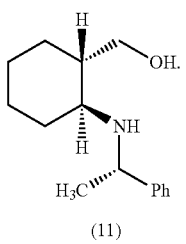

(11)

14. The process of claim 13, wherein the Lewis acid catalyst of step (f) is ytterbium trifluoromethanesulfonate.

15. The process of claim 13, wherein the selective reducing agent of step (g) is selected from sodium acetoxyborohydride and N-Selectride; and wherein the co-solvent is selected from toluene and acetonitrile.

16. The process of claim 13, wherein the base of step (h) is selected from sodium tert-butoxide and lithium hexamethyldisilazide; and wherein step (h) further comprises a solvent selected from tetrahydrofuran, tert-butanol, and a tetrahydrofuran/tert-butanol mixture.

17. The process of claim 13, wherein the (1S,2S)-ethyl 2-((S)-1-phenylethyl amino)cyclohexanecarboxylate of step (i) is reduced with a reducing agent selected from lithium borohydride, and potassium borohydride; and wherein step (i) further comprises a tetrahydrofuran co-solvent.

* * * * *

UNITED STATES PATENT AND TRADEMARK OFFICE
CERTIFICATE OF CORRECTION

| | | |
|---|---|---|
| PATENT NO. | : 8,288,565 B2 | Page 1 of 1 |
| APPLICATION NO. | : 12/837686 | |
| DATED | : October 16, 2012 | |
| INVENTOR(S) | : Chemburkar et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 7 days.

Signed and Sealed this
Twenty-ninth Day of January, 2013

David J. Kappos
*Director of the United States Patent and Trademark Office*